(12) United States Patent  
Butters et al.

(10) Patent No.: US 8,083,777 B2
(45) Date of Patent: Dec. 27, 2011

(54) SYSTEM AND METHOD FOR POLYAXIALLY ADJUSTABLE BONE ANCHORAGE

(75) Inventors: Joshua A. Butters, Chandler, AZ (US); Joseph Q Marietta, Hyde Park, UT (US)

(73) Assignee: Robert Reid, Inc., Tokyo (JP)

( * ) Notice: Subject to any disclaimer, the term of this patent is extended or adjusted under 35 U.S.C. 154(b) by 686 days.

(21) Appl. No.: 12/138,205

(22) Filed: Jun. 12, 2008

(65) Prior Publication Data

US 2008/0312696 A1 Dec. 18, 2008

Related U.S. Application Data

(60) Provisional application No. 60/944,321, filed on Jun. 15, 2007.

(51) Int. Cl.
*A61B 17/70* (2006.01)

(52) U.S. Cl. ......... 606/267; 606/265; 606/300; 606/305

(58) Field of Classification Search .......... 606/300–306, 606/308, 309, 311, 312, 323, 328, 246–278; 623/17.11–17.16
See application file for complete search history.

(56) References Cited

U.S. PATENT DOCUMENTS

| | | |
|---|---|---|
| 4,887,596 A | 12/1989 | Sherman |
| 5,005,562 A | 4/1991 | Cortel |
| 5,129,900 A | 7/1992 | Asher et al. |
| 5,207,678 A | 5/1993 | Harms et al. |
| 5,254,118 A | 10/1993 | Mirkovic |
| 5,257,993 A | 11/1993 | Asher et al. |
| 5,403,315 A | 4/1995 | Ashman et al. |
| 5,466,237 A | 11/1995 | Byrd, II et al. |
| 5,474,555 A | 12/1995 | Puno et al. |
| 5,498,262 A | 3/1996 | Bryan |
| 5,522,816 A | 6/1996 | Dinello et al. |
| 5,554,157 A | 9/1996 | Errico et al. |
| 5,562,662 A | 10/1996 | Brumfield et al. |
| 5,575,792 A | 11/1996 | Errico et al. |
| 5,591,165 A | 1/1997 | Jackson |
| 5,624,442 A | 4/1997 | Mellinger et al. |
| 5,667,507 A | 9/1997 | Corin et al. |
| 5,683,392 A | 11/1997 | Richelsoph et al. |
| 5,688,275 A | 11/1997 | Koros et al. |
| 5,707,372 A | 1/1998 | Errico et al. |
| 5,725,528 A | 3/1998 | Errico et al. |
| 5,743,907 A | 4/1998 | Asher et al. |
| 5,899,902 A | 5/1999 | Brown |
| 5,947,966 A | 9/1999 | Drewry et al. |
| 5,980,521 A | 11/1999 | Montague et al. |
| 5,980,523 A | 11/1999 | Jackson |

(Continued)

*Primary Examiner* — Thomas C. Barrett
*Assistant Examiner* — Paul J Spatafore
(74) *Attorney, Agent, or Firm* — Peter K. Johnson; James Larson; Barbara Daniels

(57) ABSTRACT

An implantable bone anchor assembly for fixing an elongated member such as a spinal rod may include a bone anchor, a coupling head configured to receive the bone anchor and the elongated member, and a locking mechanism. The locking mechanism may provide compressive force to simultaneously fix the position of the elongated member and lock out polyaxial rotation of the bone anchor relative to the coupling head. The locking mechanism may include an engagement member with an oblique surface configured to slide along an oblique surface of the coupling head into engagement with the elongated member. The bone anchor may comprise a head portion and a threaded portion which may be coupled with the coupling head and joined together during manufacture. The assembly may further include a pin and/or a collar to retain the bone anchor. The bone anchor may be side-loaded into the coupling head.

22 Claims, 25 Drawing Sheets

U.S. PATENT DOCUMENTS

| | | |
|---|---|---|
| 6,015,409 A | 1/2000 | Jackson |
| 6,039,738 A | 3/2000 | Sanders et al. |
| 6,050,997 A | 4/2000 | Mullane |
| 6,080,156 A | 6/2000 | Asher et al. |
| 6,083,226 A | 7/2000 | Fiz |
| 6,083,227 A | 7/2000 | Saurat et al. |
| 6,113,600 A | 9/2000 | Drummond et al. |
| 6,136,003 A | 10/2000 | Hoeck et al. |
| 6,179,838 B1 | 1/2001 | Fiz |
| 6,217,578 B1 | 4/2001 | Crozet et al. |
| 6,283,967 B1 | 9/2001 | Troxell |
| 6,402,751 B1 | 6/2002 | Hoeck et al. |
| 6,413,257 B1 | 7/2002 | Lin et al. |
| 6,432,108 B1 | 8/2002 | Burgess et al. |
| 6,485,491 B1 | 11/2002 | Farris et al. |
| 6,488,681 B2 | 12/2002 | Martin et al. |
| 6,520,962 B1 | 2/2003 | Taylor et al. |
| 6,554,834 B1 | 4/2003 | Crozet et al. |
| 6,602,253 B2 * | 8/2003 | Richelsoph et al. .......... 606/252 |
| 6,641,583 B2 | 11/2003 | Shluzas et al. |
| 6,660,004 B2 | 12/2003 | Barker et al. |
| 6,685,705 B1 | 2/2004 | Taylor |
| 6,716,213 B2 | 4/2004 | Shitoto |
| 6,858,030 B2 | 2/2005 | Martin |
| 6,958,066 B2 * | 10/2005 | Richelsoph et al. .......... 606/252 |
| 6,960,212 B2 * | 11/2005 | Richelsoph et al. .......... 403/342 |
| 7,081,116 B1 | 7/2006 | Carly |
| 7,090,674 B2 | 8/2006 | Doubler et al. |
| 7,479,156 B2 * | 1/2009 | Lourdel et al. ................ 606/266 |
| 7,717,938 B2 * | 5/2010 | Kim et al. ..................... 606/250 |
| 7,789,897 B2 * | 9/2010 | Sanders ........................ 606/278 |
| 7,833,250 B2 * | 11/2010 | Jackson ........................ 606/270 |
| 2005/0187548 A1 * | 8/2005 | Butler et al. .................... 606/61 |
| 2006/0116676 A1 * | 6/2006 | Gradel et al. ................... 606/61 |
| 2006/0235389 A1 * | 10/2006 | Albert et al. .................... 606/61 |

* cited by examiner

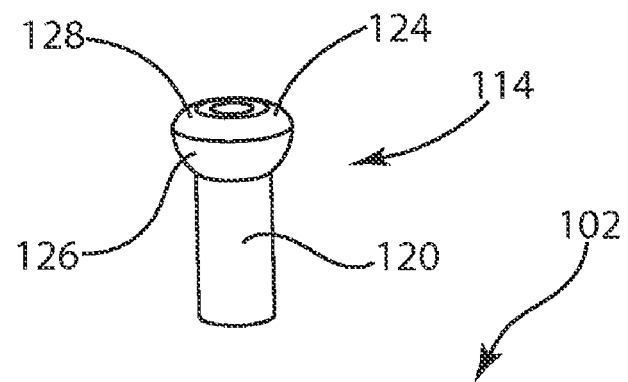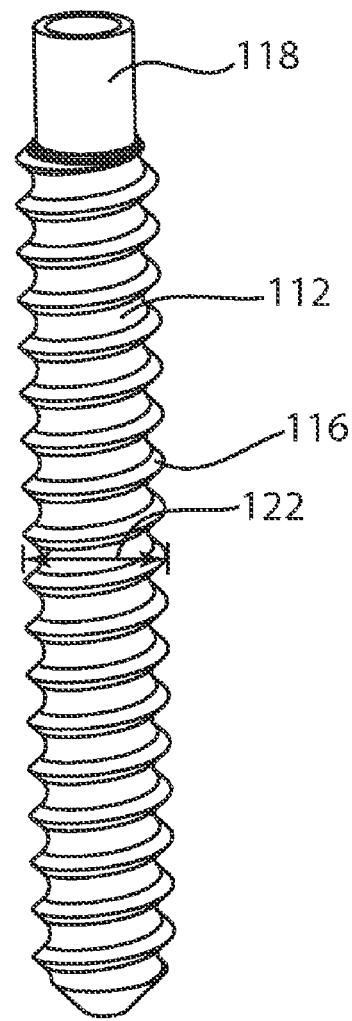
Fig. 2

SYSTEM AND METHOD FOR POLYAXIALLY ADJUSTABLE BONE ANCHORAGE

CROSS-REFERENCE TO RELATED APPLICATIONS

This application claims the benefit of the following, which are incorporated herein by reference:

U.S. Provisional Patent Application No. 60/944,321, filed Jun. 15, 2007, and is entitled WEDGE CLAMP POLYAXIAL PEDICLE SCREW;

U.S. Provisional Patent Application No. 61/029,467, filed Feb. 18, 2008, and is entitled MODULAR POLYAXIAL PEDICLE SCREW; and U.S. Provisional Patent Application No. 61/031,276, filed Feb. 25, 2008, and is entitled SIDE LOADING POLYAXIAL PEDICLE SCREW.

BACKGROUND OF THE INVENTION

The Field of the Invention

The present invention relates to orthopaedics, and more particularly, to systems and methods for implantable bone anchor and rod assemblies to provide spinal support.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 2 illustrates an exploded perspective view of the bone anchor of FIG. 1;

DETAILED DESCRIPTION OF THE PREFERRED EMBODIMENTS

The present invention relates to systems and methods for bone anchor and rod assemblies for providing spinal support. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

One embodiment of the present invention includes a bone anchor having a threaded section and an at-least partially spherical head, a rod coupling member that has polyaxial adjustability with the spherical bone anchor head, a compression element, an engagement member, and a elongated member, which may be a spinal rod. A method of clamping to the spinal rod consists of a set screw located laterally in the pedicle screw assembly with respect to the implant rod, but still within the rod coupling head. This screw acts on a wedge-shaped clamping engagement member that rests on an inclined plane feature on one side of the top of the rod coupling head. The act of tightening the set screw provides a mechanically advantaged force that drives the wedge-shaped clamp into the implant rod, which in turn, transmits a force to the bone anchor head, which presses against the spherical cavity in the rod coupling head. This action secures the rod in place while also locking the position/orientation of the rod coupling head relative to the bone anchor head. Locating the clamping member/set screw laterally may greatly reduce the posterior profile of the pedicle screw implant located above the rod.

Figure 1:
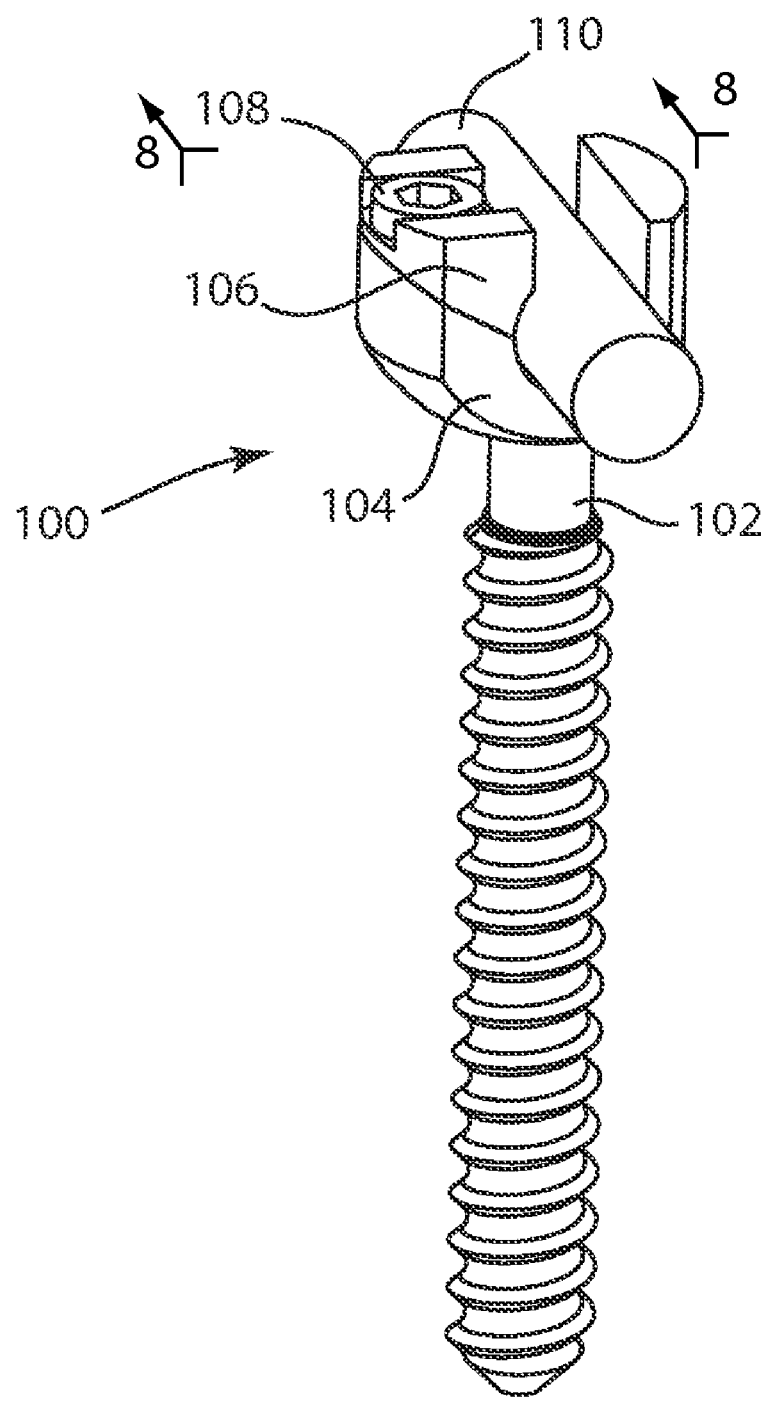
FIG. 1 illustrates a perspective view of a bone anchor assembly comprising a bone anchor, a coupling head, an engagement member, and a locking member, and a spinal rod clamped in the bone anchor assembly.

FIGS. 1-8 illustrate an embodiment of a bone anchor assembly with a wedge-shaped clamping engagement member, and a spinal rod. Referring to FIG. 1, bone anchor assembly 100 includes a bone anchor 102, a coupling head 104, a wedge-shaped clamping member 106, and a locking member which is a set screw 108. A spinal rod 110 is received by the coupling head 104 and rigidly clamped by the clamping member 106. In addition to the spinal rod 110 illustrated, other rod-like elongated members may be received and clamped by the assembly 100, including facet joint replacement components, spinal fusion devices, or other orthopaedic devices with a rod-like attachment portion shaped to be received in a coupling member such as coupling head 104 or other coupling heads disclosed within.

Referring to FIG. 2, bone anchor 102 comprises a threaded portion 112 and a head portion 114. The threaded portion 112 includes threads 116 which may extend entirely or partially along the threaded portion 112. A first fitting feature 118 is located on the threaded portion 112, and shaped to mate with a second fitting feature 120 situated on the head portion 114. A maximum diameter 122 of the threaded portion 112 is measured normal to the longitudinal axis of the threaded portion, from the maximum lateral extension of the thread on one side to the maximum lateral extension of the thread on the opposite side. The head portion 114 further comprises a head 124 which may be at least semispherical, comprising a semispherical shoulder 126 and a crown 128. A "semispherical" surface is a concave or convex surface that contains at least some three dimensional portion of the outer surface of a sphere.

The first and second fitting features 118, 120 are shaped to be joined by press fitting, welding, brazing, or other methods well known in the art, thus joining the independent head 114 and threaded 112 portions into a single, permanently joined piece. The bone anchor 102 may be cannulated throughout such that a lumen extends through its entire length. Advantageously, during manufacture the head portion 114 may be assembled with the coupling head 104 such that the second fitting feature 120 extends distal of the coupling head 104. The second fitting feature 120 is coupled with the first fitting feature on the threaded portion 118, and joined as described. Thus assembled the bone anchor 102 and coupling head 104 form a partial bone anchor assembly 101.

Figure 3A:
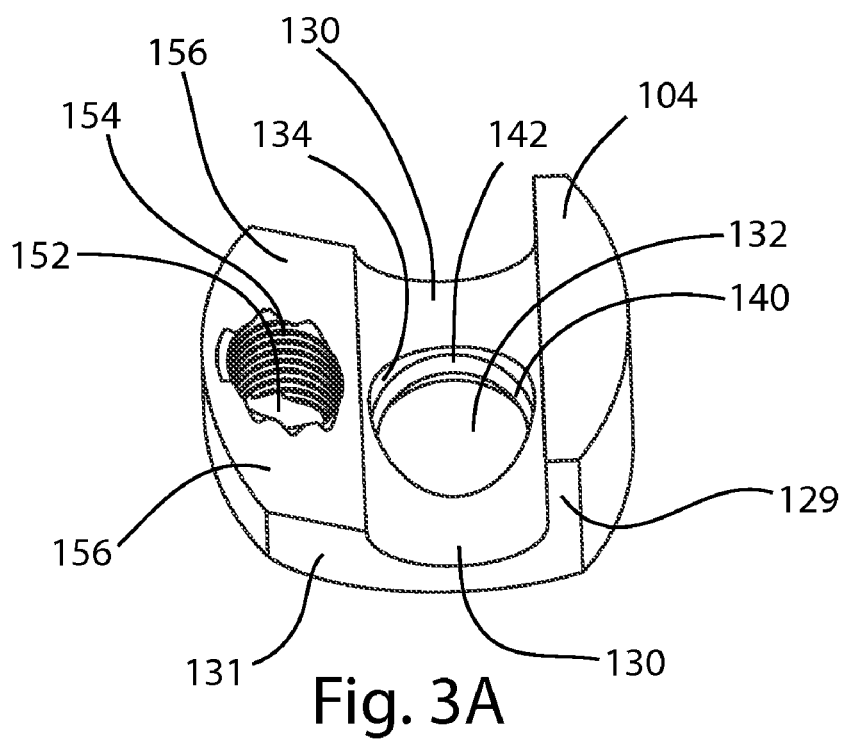
FIG. 3A illustrates a perspective view of the coupling head of FIG. 1.
Figure 3B:
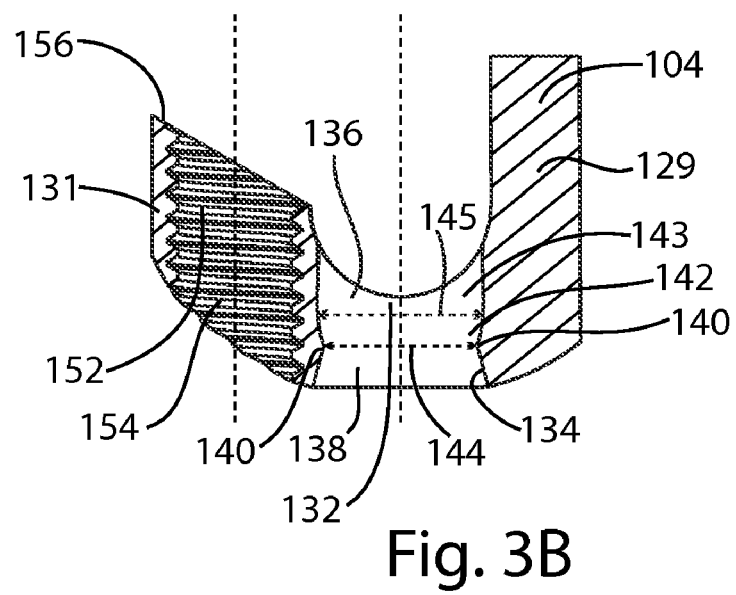
FIG. 3B illustrates a cross-sectional view of the coupling head of FIG. 1.

FIG. 3A is a perspective view of coupling head 104, while FIG. 3B is a transverse cross-section of the member. Coupling head 104 may be monolithic and may be generally U-shaped, with a first support body wall and a second support wall 131 flanking a channel 130. The channel 130 is semi-cylindrical and shaped to receive the spinal rod 110 (seen in FIG. 1). A first bore 132, encircled by a bore surface 134, extends through the member 104, perpendicular to the channel 130. The first bore 132 is shaped to receive the bone anchor 102, and includes a proximal bore portion 136 and a distal bore portion 138 which are delimited by a ridge 140 which protrudes from the bore surface 134. A semispherical seat 142 is formed in the proximal bore portion 136 and is immediately proximal to the ridge 140. The proximal bore portion encircles a spherical cavity 143. A minimum diameter 144 of the first bore 132 is measured normal to the longitudinal axis of the first bore 132, from one location on the ridge 140 directly across the bore to the opposite side. A maximum diameter 145 of the spherical cavity 143 is measured normal to the longitudinal axis of the first bore 132, from the widest part of the spherical cavity across to the widest part on the opposite side. The bore 132 is shaped to receive the bone anchor 102 such that the head 124 is contained in the proximal bore portion 136, and the semispherical shoulder 124 may rest against the semispherical seat 142 in a plurality of relative orientations. The proximal 136 and distal 138 bore portions are sized and shaped so that when the head 124 is contained in the proximal bore portion 136, but before tightening of the set screw 108, the bone anchor 102 may polyaxially rotate relative to the coupling head 104.

A second bore 152, independent and offset from the first bore 132, extends through the second support wall 131 of the coupling head 104. The second bore 152 may be parallel to the first bore 132 and perpendicular to the channel 130. The second bore 152 is encircled by a threaded surface 154 and is configured to receive the set screw 108. A second oblique surface 156 occupies a proximal side of the second support wall 131.

Figure 4A:
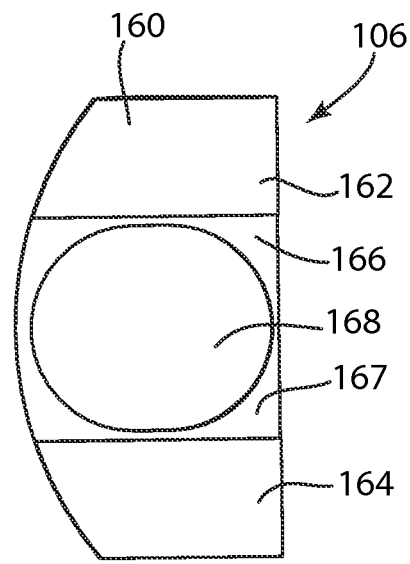
FIG. 4A illustrates a posterior view of the engagement member of FIG. 1.
Figure 4B:
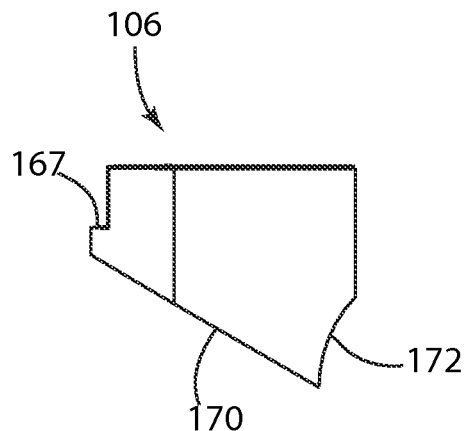
FIG. 4B illustrates a side view of the engagement member of FIG. 1.
Figure 4C:
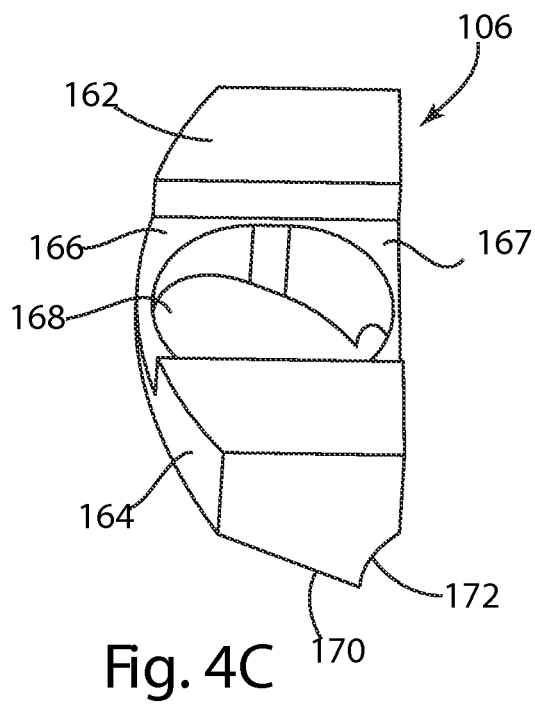
FIG. 4C illustrates a perspective posterior view of the engagement member of FIG. 1.
Figure 4D:
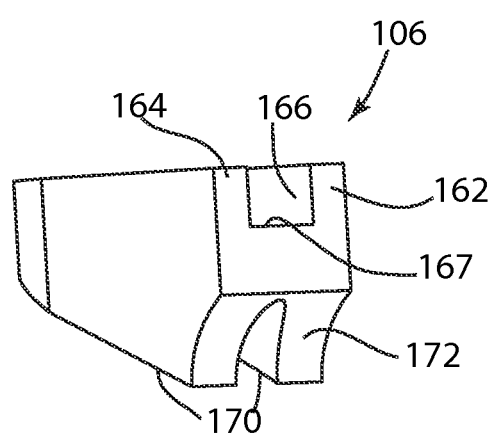
FIG. 4D illustrates a perspective side view of the engagement member of FIG. 1.

Referring to FIGS. 4A-C, several views of the clamping member 106 are shown. Clamping member 106, in combination with set screw 108, can form a locking mechanism which can be actuated to lock the spinal rod in a fixed position relative to the coupling head 104. The clamping member 106 is generally wedge-shaped and may also be termed an engagement member. The clamping member 106 is configured to slide along the second oblique surface 156 of the coupling head 104 into engagement with the spinal rod 110, when the set screw 108 is actuated. The clamping member 106, coupling head 104 and set screw 108 are sized and shaped to create a low profile spinal rod connection. By locating the set screw 108 in a lateral position relative to the rod a reduced posterior profile may be created in comparison to an assembly with a proximally positioned set screw.

Clamping member 106 comprises a wedge body 160 with a first body wall 162 and a second body wall 164. The body walls 162, 163 flank a recessed area 166 with a recessed surface 167. Extending distally from the recessed surface 167 is an aperture 168. Distal to the walls 162, 164 and aperture 168 is a first oblique surface 170. At the junction of the first oblique surface 170 and the walls 162, 164 is an engagement surface 172, which may be curved to fit around a portion of the spinal rod 110. The aperture 168 is substantially oval in shape and sized to receive the set screw 108. The first oblique surface 170 may be shaped to complement the second oblique surface 156 of the coupling head 104.

Figure 5:
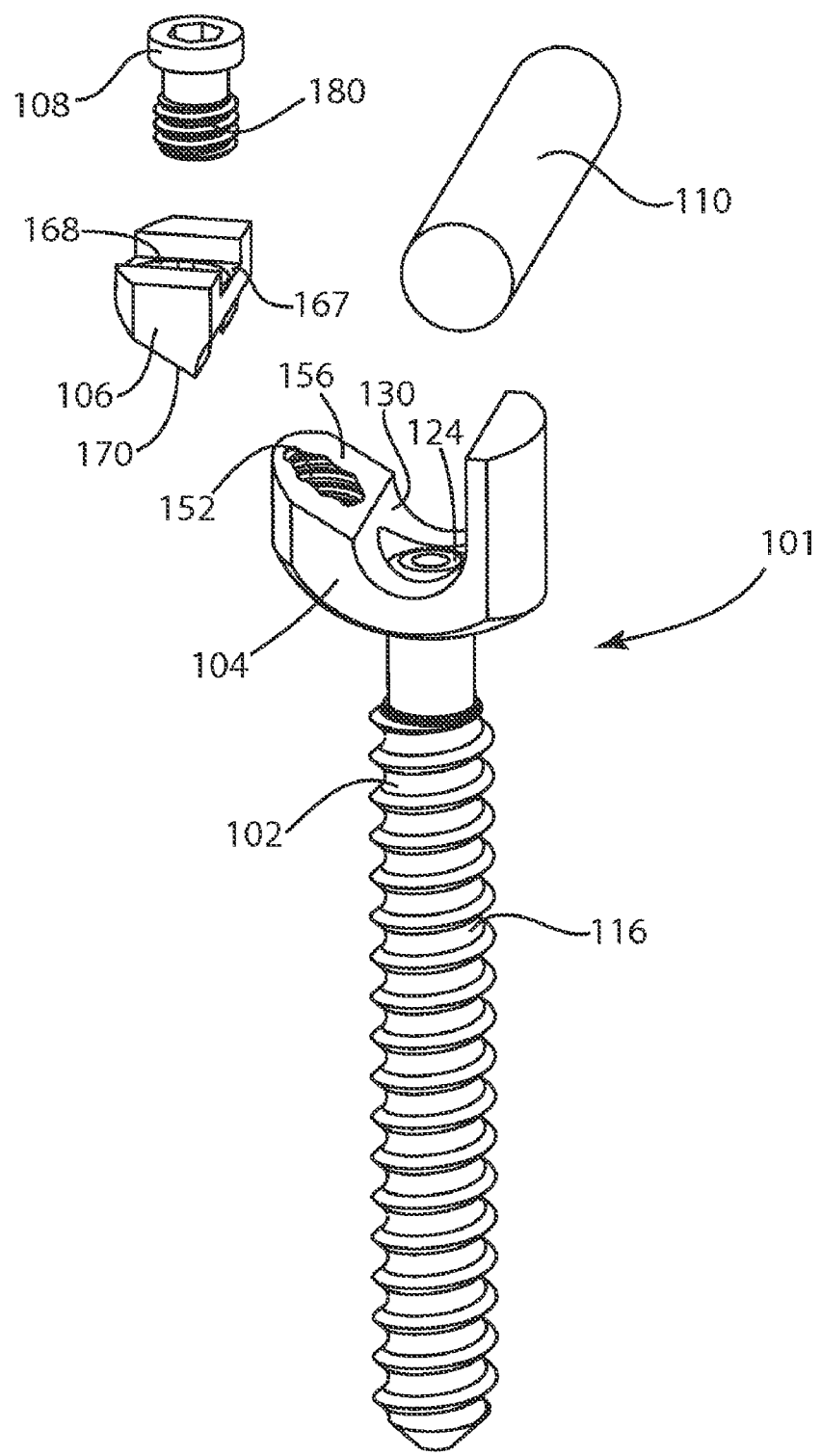
FIG. 5 illustrates an exploded perspective view of the bone anchor assembly and spinal rod of FIG. 1.
Figure 6:
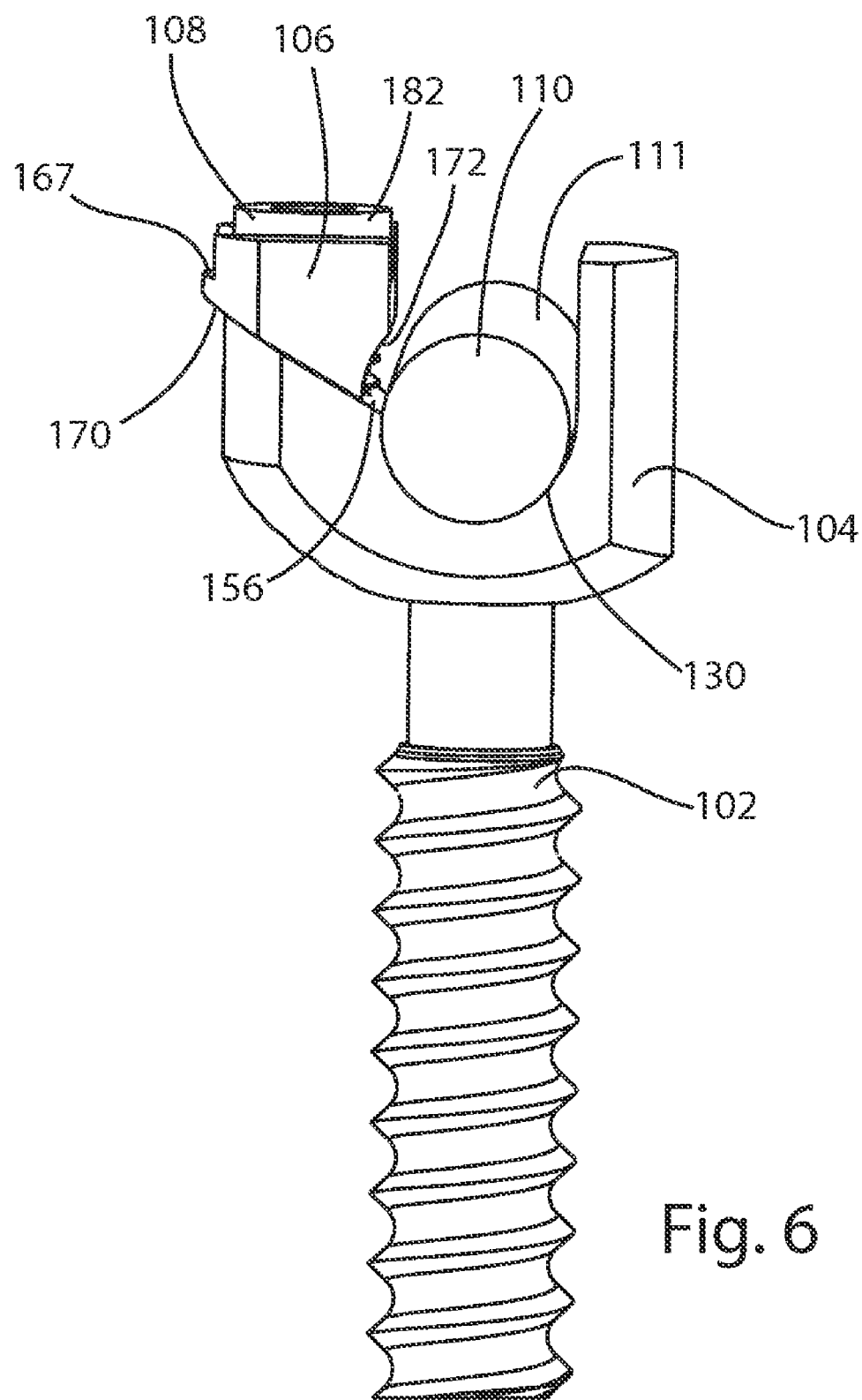
FIG. 6 illustrates a partial side view of the bone anchor assembly and spinal rod of FIG. 1 with the engagement member in partial engagement with the coupling head and the spinal rod.
Figure 7:
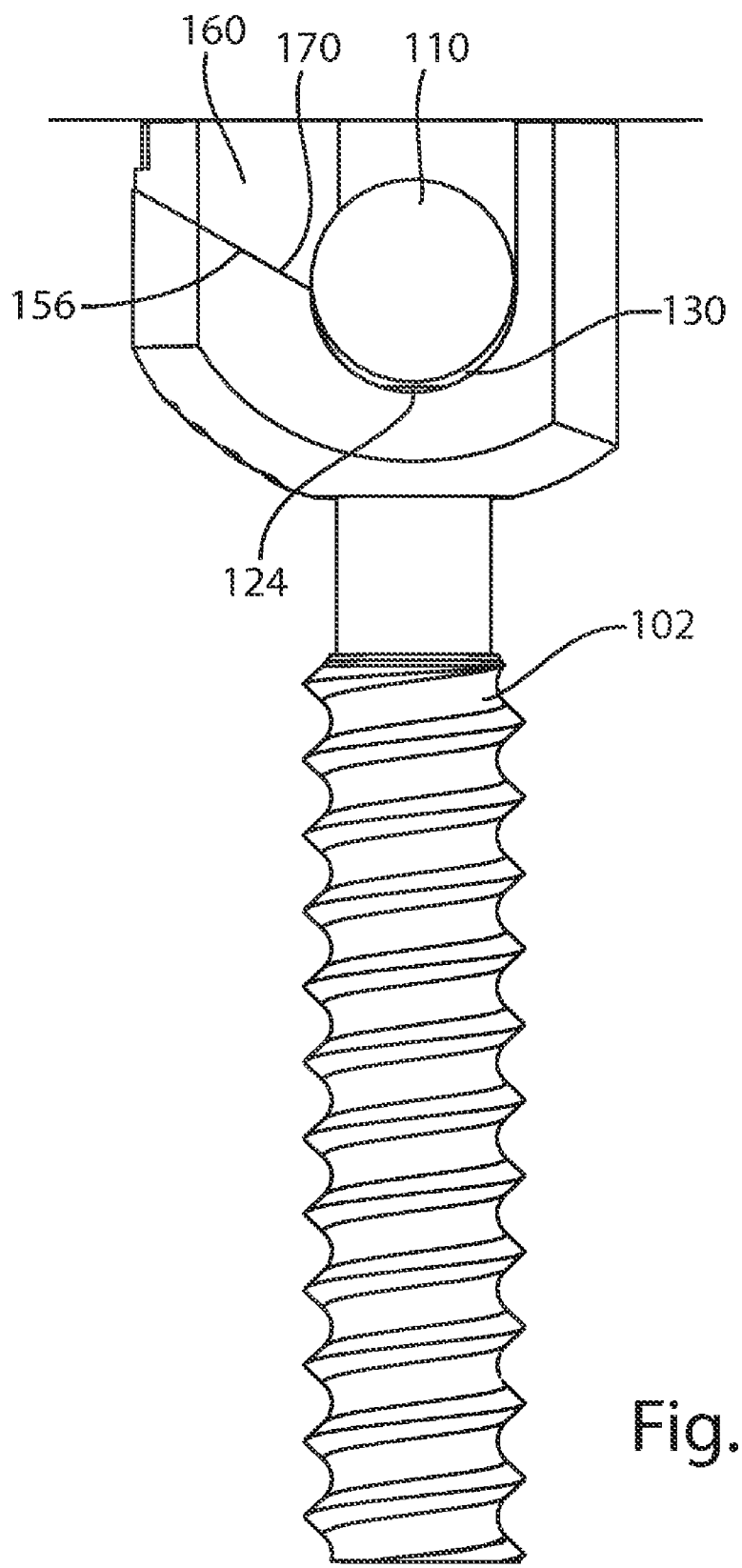
FIG. 7 illustrates a partial side view of the bone anchor assembly and spinal rod of FIG. 6 with the engagement member in engagement with the coupling head and the spinal rod.

FIGS. 5-7 illustrate one method of assembling spinal rod 110 with bone anchor assembly 100. Referring to FIG. 5, a partially exploded view of bone anchor assembly 100 and spinal rod 110 are shown. As previously set forth, during manufacture bone anchor 102 may be assembled with coupling head 104, to form partial bone anchor assembly 101. Following bone preparation, which may include placement of a guide wire or other guiding feature, the threaded portion 116 of partial bone anchor assembly 101 is anchored in the bone. Coupling head 104 may be polyaxially adjusted relative to the head portion 114 of the bone anchor 102 to attain a preferred orientation.

Figure 8:
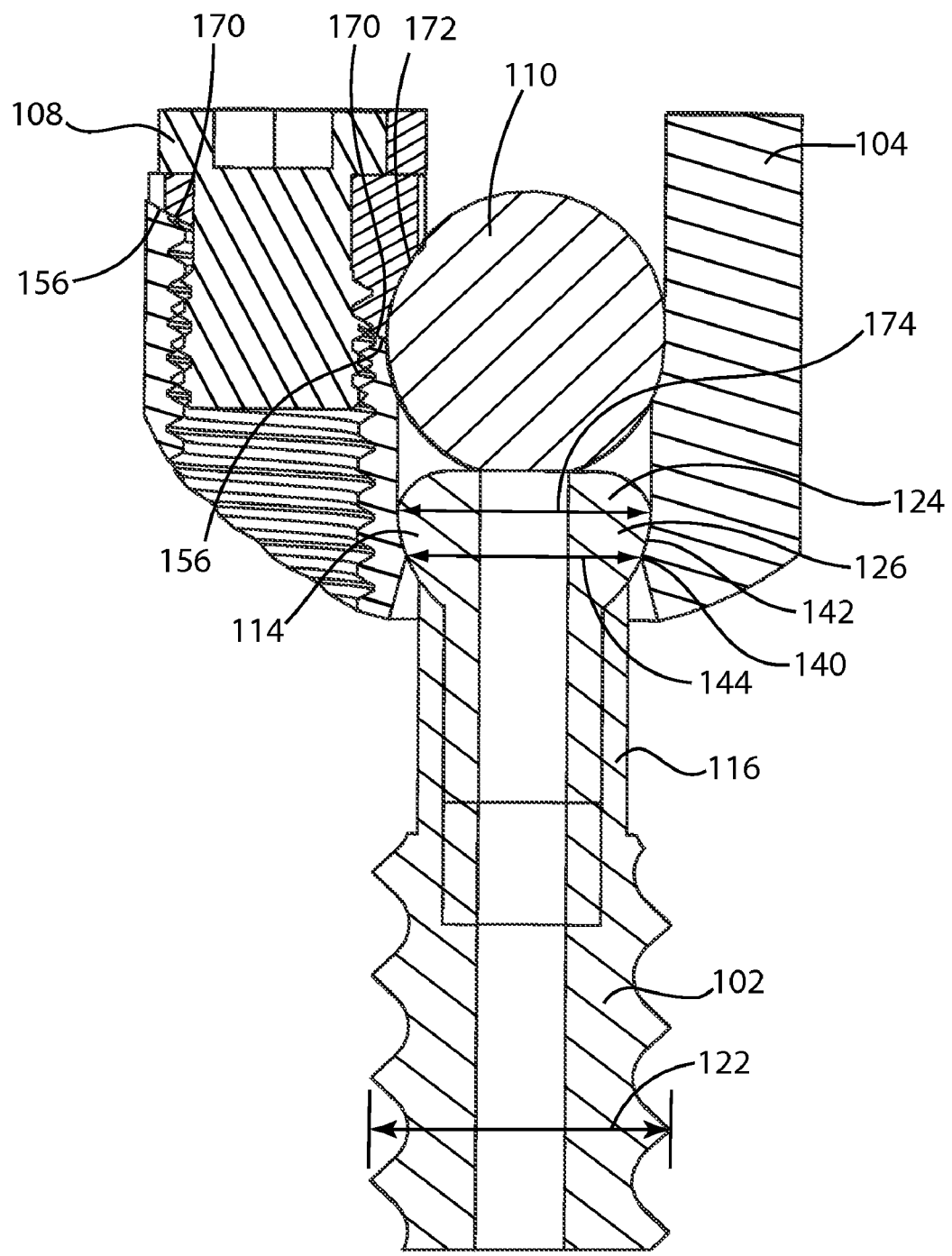
FIG. 8 illustrates a partial cross-sectional view of the bone anchor assembly and spinal rod of FIG. 7.

Referring also to FIG. 6, an attachment portion 111 of the spinal rod 110 is placed in the channel 130. The attachment portion 111 contacts the head 124 of the bone anchor 102. A threaded portion 180 of set screw 108 is received through the aperture 168 of the wedge member 106. After passing through the aperture 168, the threaded portion 180 is received in the second bore 152, and the threads engage with the threaded wall 154. As the set screw 108 is actuated by turning, a head 182 of the set screw 108 engages the recessed surface 167 of the wedge member 106, urging the wedge member toward the spinal rod 110. The wedge member 106 is drawn transverse to the axis of the set screw 108, and the first oblique surface 170 of the wedge member 106 moves transversely along the second oblique surface 156 of the coupling head 104. As seen in FIGS. 7 and 8, actuation of the set screw 108 may continue until the engagement surface 172 presses against the spinal rod 110, rigidly clamping the rod 110 in the channel 130. The spinal rod transmits a force to the head 124 of the bone anchor 102, and the semispherical shoulder 126 is pressed against the semispherical seat 142 of the coupling head 104. Thus, the position and orientation of both the spinal rod 110 and the bone anchor 102 relative to the coupling head 104 are locked out.

FIG. 8 is an enlarged cross-sectional view of the bone anchor assembly 100 locked to the spinal rod 110. As set forth previously, during manufacture the head 114 and threaded portions 116 of bone anchor 102 may be coupled with coupling head 104 and joined such that the head portion 114 is retained proximal to the ridge 140 of the first bore 132, and the threaded portion extends distal to the bore 132. Since the bone anchor 102 and coupling head 104 are thus pre-assembled, during implantation the bone anchor 102 need not be top- or bottom-loaded into the coupling head 104. As a result, the maximum diameter 122 of the threaded portion 116 of the bone anchor 102 may be greater than the minimum diameter 144 of the first bore. Similarly, a maximum diameter 174 of the head portion 114 of the bone anchor 102 may be greater than the minimum diameter 144 of the first bore. The maximum diameter 174 of the head portion 114 of the bone anchor 102 may be less than the maximum diameter 122 of the threaded portion 116. The maximum diameter 145 of the spherical cavity 143 may be less than the maximum diameter 122 of the threaded portion 116.

Another embodiment of the present invention includes a bone anchor having a threaded section and an independent at-least partially spherical head configured to be joined to the threaded section, a rod coupling head that has polyaxial adjustability with the spherical bone anchor head, a compression element, and an implant rod. During manufacture, the bone anchor is assembled with the rod coupling head such that the bone anchor head is received by the rod coupling head, and joined to the threaded section so that the threaded section extends distally of the rod coupling head. A method of clamping to the implant rod consists of a set screw located superior in the pedicle screw assembly with respect to the implant rod. This screw acts on directly on the implant rod. The act of tightening the set screw provides a mechanically advantaged force that drives the inferior set screw surface into the implant rod, which in turn, transmits a force to the bone anchor head, which presses against the spherical cavity in the rod coupling head. This action secures the rod in place while also locking the position and/or orientation of the rod coupling head relative to the bone anchor head. This assembly allows the threaded portion of the bone anchor to be bottom-loaded during manufacture and therefore the spherical head is not required to be larger in diameter than the screw threads, and accordingly, the matching spherical cavity in the rod coupling head can be smaller. This may provide substantial reduced profile advantages for the rod coupling head and overall pedicle screw assembly.

Figure 9:
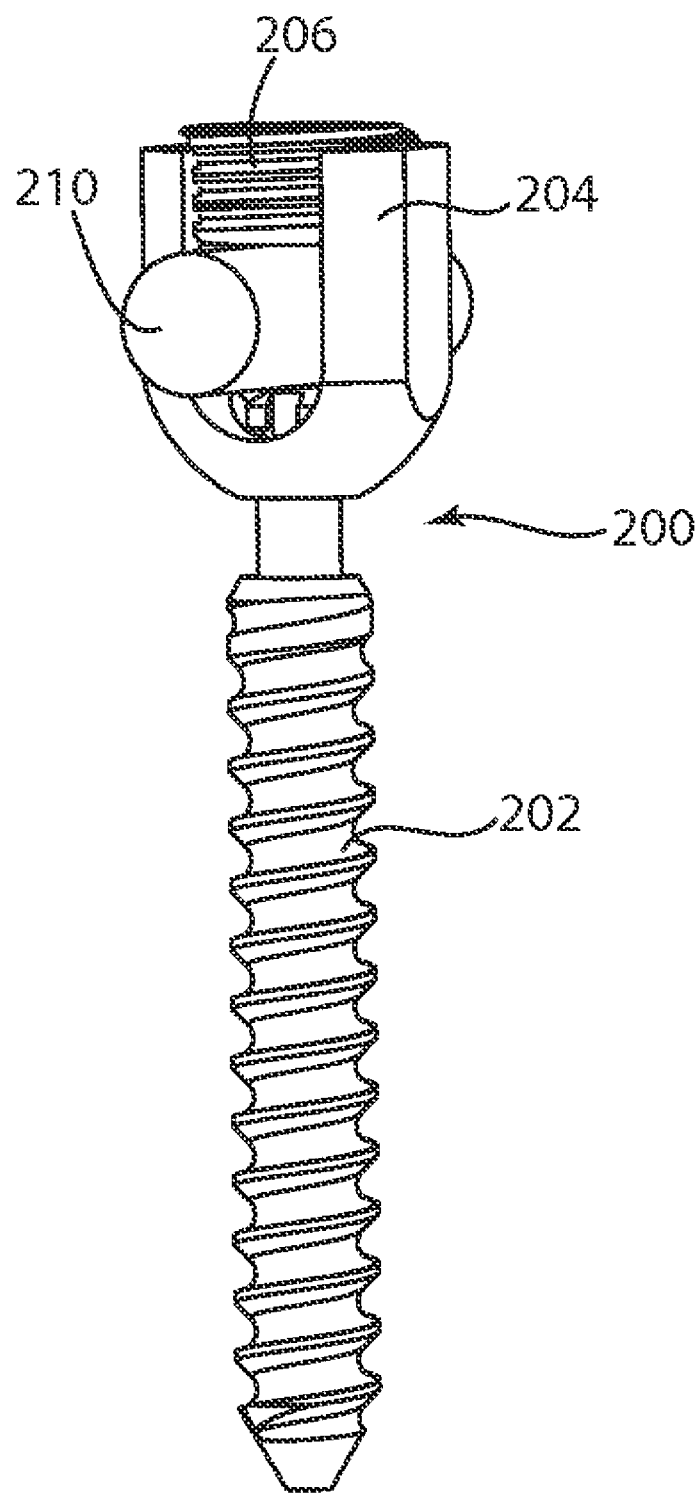
FIG. 9 illustrates a perspective view of an alternative embodiment of a bone anchor assembly comprising a bone anchor, a coupling head, and a locking member, and a spinal rod clamped in the bone anchor assembly.

FIGS. 9-12 illustrate an alternative embodiment of a bone anchor assembly configured to hold an elongated member in a fixed position. Referring to FIG. 9, a bone anchor assembly 200 is shown with a spinal rod 210. Bone anchor assembly 200 comprises a bone anchor 202, coupling head 204, and compression member, or set screw, 206. Bone anchor 202 is configured to be anchored in a pedicle of a vertebra, or in another bone. Coupling head 204 may be coupled with the bone anchor 202 during manufacture, and is shaped to receive a spinal rod 210 or other elongated rod-like member. Set screw 206 is configured to be actuated to engage with the coupling head 204 to provide force on the spinal rod 210 and in turn the bone anchor 202, to lock out polyaxial motion between the bone anchor 202 and the coupling head 204, and to fix the position of the spinal rod 210 relative to the assembly 200.

Figure 10:
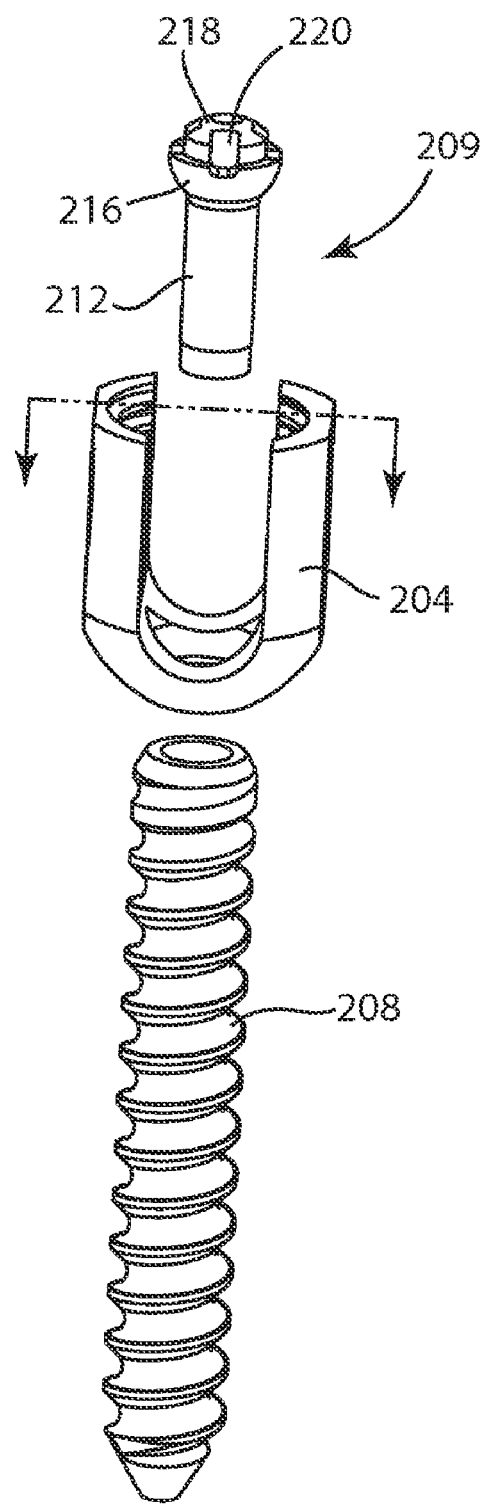
FIG. 10 illustrates an exploded perspective view of the bone anchor and coupling head of FIG. 9.

Referring to FIG. 10, bone anchor 202 comprises a threaded portion 208 and a head portion 209. The threaded portion 208 may be partially or entirely threaded. The head portion 209 comprises an elongated neck 212 and a head 214. The head 214 further comprises a semispherical shoulder 216 and a crown 218. One or more driver features 220 may be included in the head 214 to cooperate with a driver or other tool configured to grip, drive or otherwise manipulate the bone anchor 202. The bone anchor 202 may be cannulated throughout.

Figure 11:
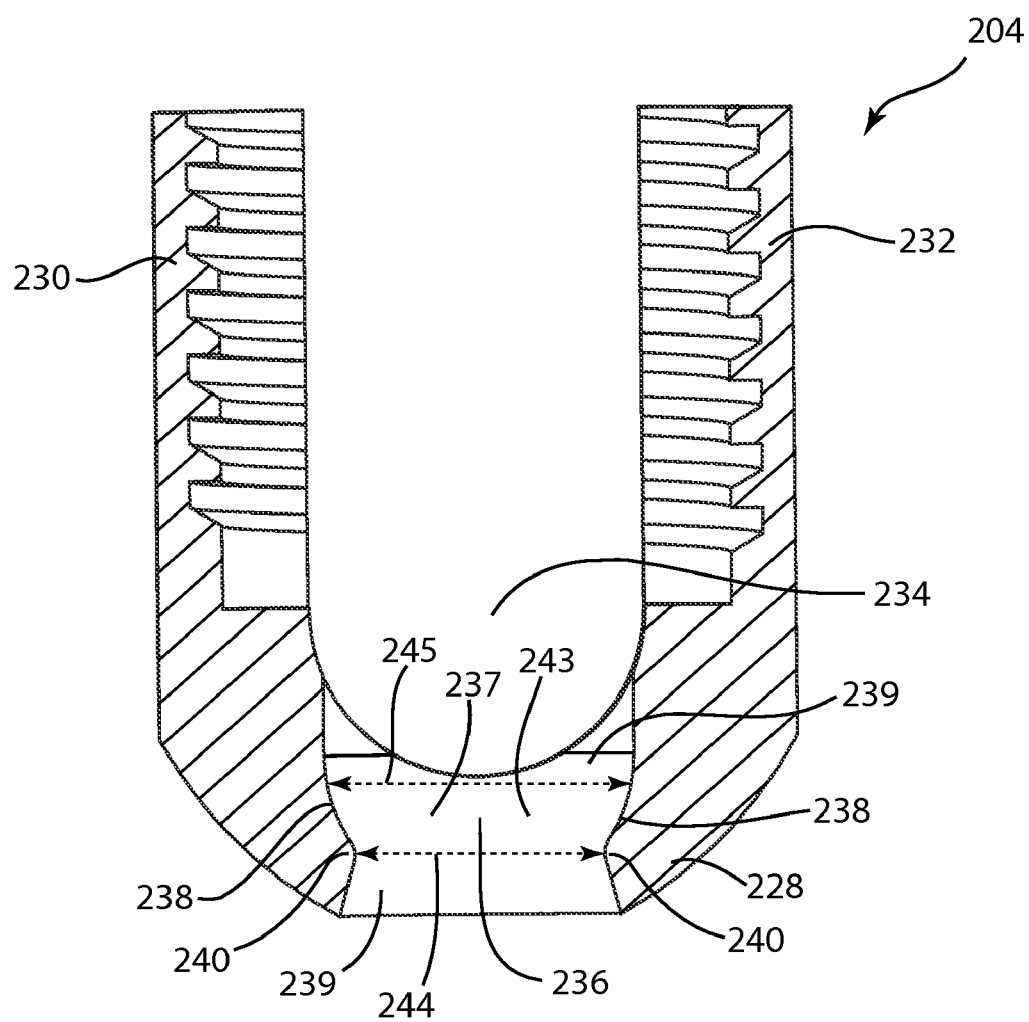
FIG. 11 illustrates a cross-sectional view of the coupling head of FIG. 10.

Referring to FIG. 11, coupling head 204 is generally tulip-shaped, with a semispherical base 228, and a first support wall 230 and a second support wall 232 flanking a U-shaped channel 234. Distal and perpendicular to the channel 234, a bore 236 extends through the semispherical base 228. The bore 236 is shaped to receive the bone anchor 202, and includes a proximal bore portion 237 and a distal bore portion 239 which are delimited by a ridge 240 which is an annular protrusion from the semispherical base 228 and defines a location of minimum diameter of the bore 236. A semispherical seat 238 is formed in the proximal bore portion 237 and is immediately proximal to the ridge 240. The proximal bore portion 237 encircles a spherical cavity 243. A minimum diameter 244 of the bore 236 is measured normal to the longitudinal axis of the bore 236, from one location on the ridge 240 directly across the bore to the opposite side. A maximum diameter 245 of the spherical cavity 243 is measured normal to the longitudinal axis of the bore 236, from the widest part of the spherical cavity across to the widest part on the opposite side. A portion of the interior surfaces of the first 230 and second 232 support walls are threaded to receive the set screw 206 (not shown).

Referring to FIGS. 10 and 11, head portion 209 is configured to be coupled with coupling head 204 and joined to threaded portion 208 during the manufacturing process. Head portion 209 may be received by bore 236 in coupling head 204 such that head 214 is retained proximal of a location of minimum diameter of the bore, and neck 212 extends through the bore and distal to the bore. Neck 212 is coupled with the threaded portion 208 distal to the bore 236, and permanently joined to the threaded portion by means which may include welding, grazing, press-fit, or other methods. After joining but before lockout of the assembly, bone anchor 202 may freely polyaxially rotate relative to the coupling head 204.

Figure 12:
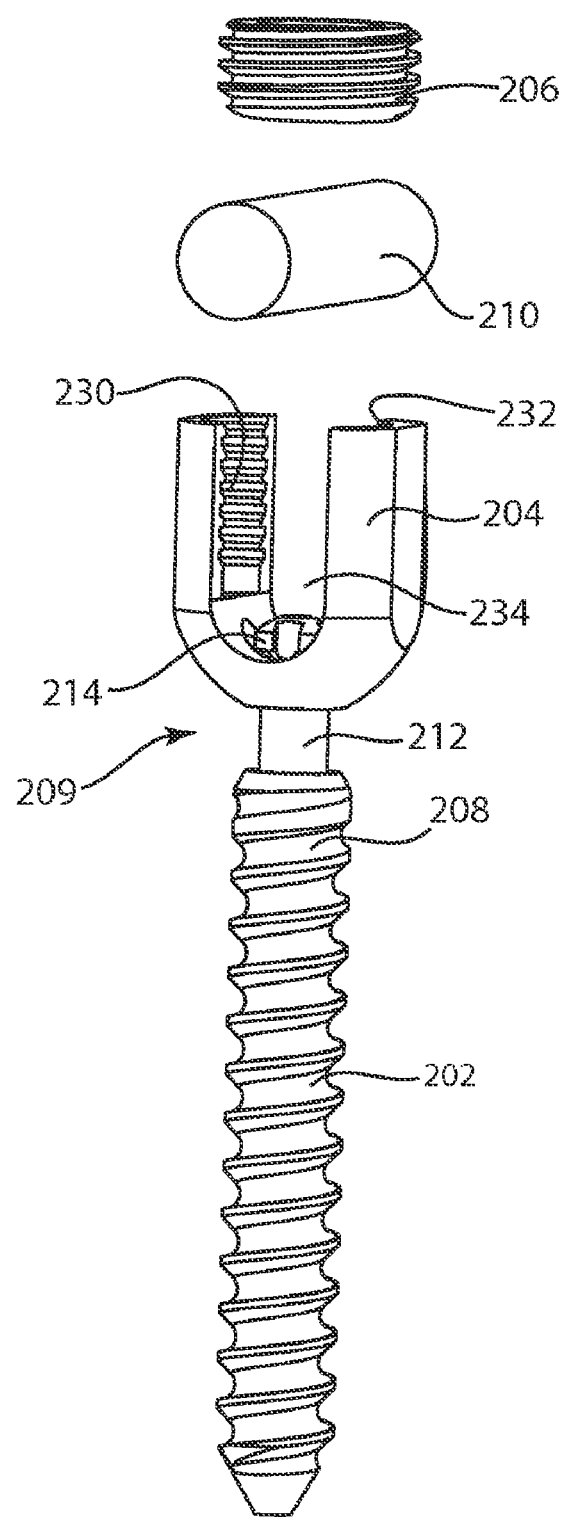
FIG. 12 illustrates a partially exploded perspective view of the bone anchor assembly and spinal rod of FIG. 9.

Referring to FIGS. 11 and 12, bone anchor 202, coupled with coupling head 204 as set forth previously, may be anchored in a pedicle of a vertebra or another bone. Coupling head 204 may be polyaxially rotated to a preferred orientation relative to the bone anchor 202. Spinal rod 210 or another elongated rod-like portion of an implant may be positioned in the channel of the coupling head 204. Set screw 206 is actuated to engage with the threaded surfaces of support walls 230, 232. As the set screw 206 is turned it is driven into contact with the spinal rod 210, and the spinal rod in turn transmits a force to the head 214, which presses against the semispherical seat 238 in the bore 236. The spinal rod 210 is thus secured in position relative to the coupling head 204 and the orientation of the coupling head 204 relative to the bone anchor 202 is fixed.

Figure 13:
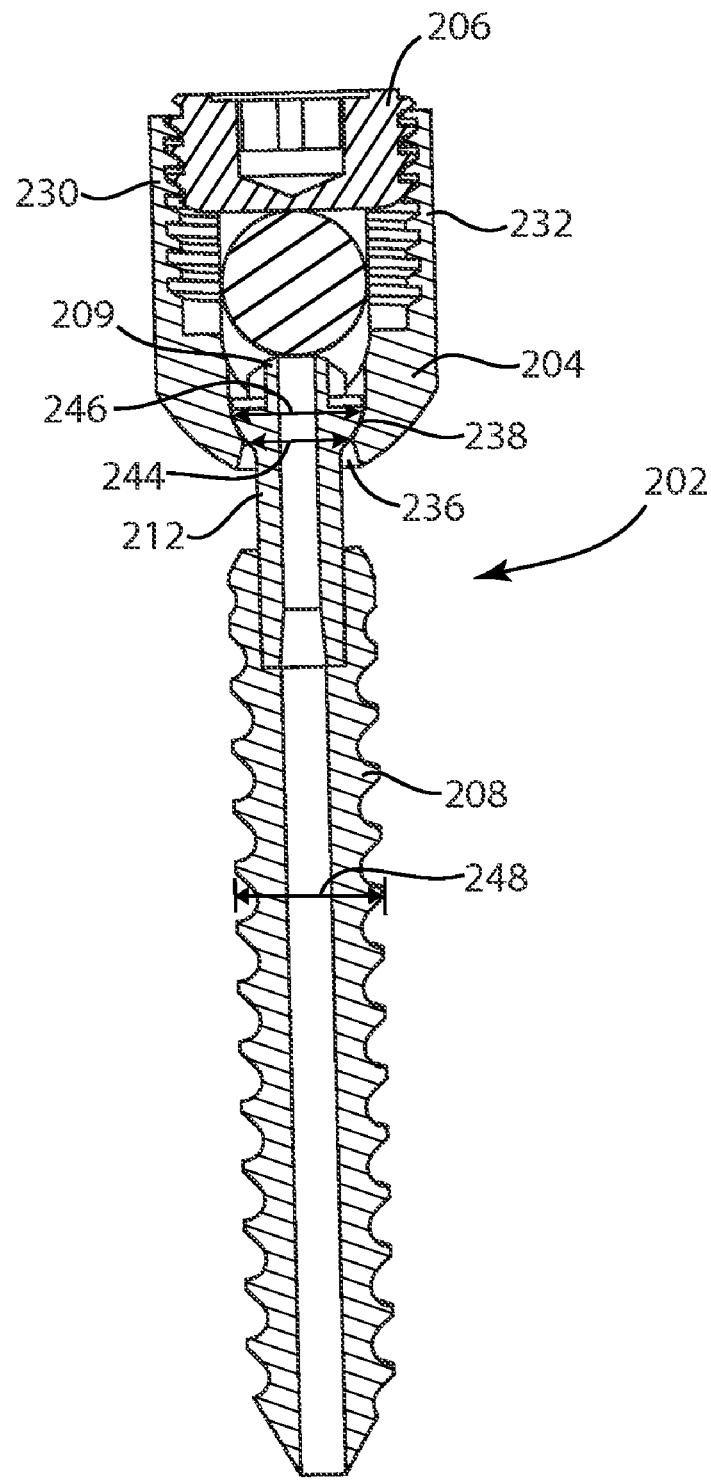
FIG. 13 illustrates a cross-sectional view of the bone anchor assembly and spinal rod of FIG. 9.

Referring to FIG. 13, a cross-sectional view of the bone anchor assembly 200 assembled with a spinal rod 210 is shown. Because the bone anchor 202 is pre-assembled with the coupling head 204, the bone anchor does not have to be top-loaded into coupling head, and a maximum diameter 246 of the head portion 209 may be less than a maximum diameter 248 of the threaded portion 208. Similarly, the maximum diameter 248 of the threaded portion 208 may be greater than the minimum diameter 244 of the bore 236. The maximum diameter 246 of the head portion 209 may be greater than a minimum diameter 244 of the bore 236. Also, the maximum diameter 245 of the spherical cavity 243 may be less than the maximum diameter 248 of the threaded portion 208.

Another embodiment of the present invention includes a bone anchor having a threaded section and an at-least partially spherical head, a rod coupling head that has polyaxial adjustability with the spherical bone anchor head, a compression element, and a spinal rod. A collar or ring component may be used to further strengthen the rod coupling head after assembly with the bone anchor and can be fixed via a press fit, weld, threads or any other means well known in the art. The rod coupling head may include a keyhole-shaped slot which allows the bone anchor to be side-loaded into the rod coupling head. The method of clamping to the spinal rod consists of a set screw located superior in the pedicle screw assembly with respect to the implant rod. This screw acts on directly on the implant rod. The act of tightening the set screw provides a mechanically advantaged force that drives the inferior set screw surface into the implant rod, which in turn, transmits a force to the bone anchor head, which presses against the spherical cavity in the rod coupling head. This action secures the rod in place while also locking the position/orientation of the rod coupling head relative to the bone anchor head. Using a side-loaded bone anchor element does not require the spherical head to be larger in diameter than the screw threads, and accordingly, the matching spherical cavity in the rod coupling head can be smaller. This may provide substantial reduced profile advantages for the rod coupling head and overall pedicle screw assembly.

Figure 14:
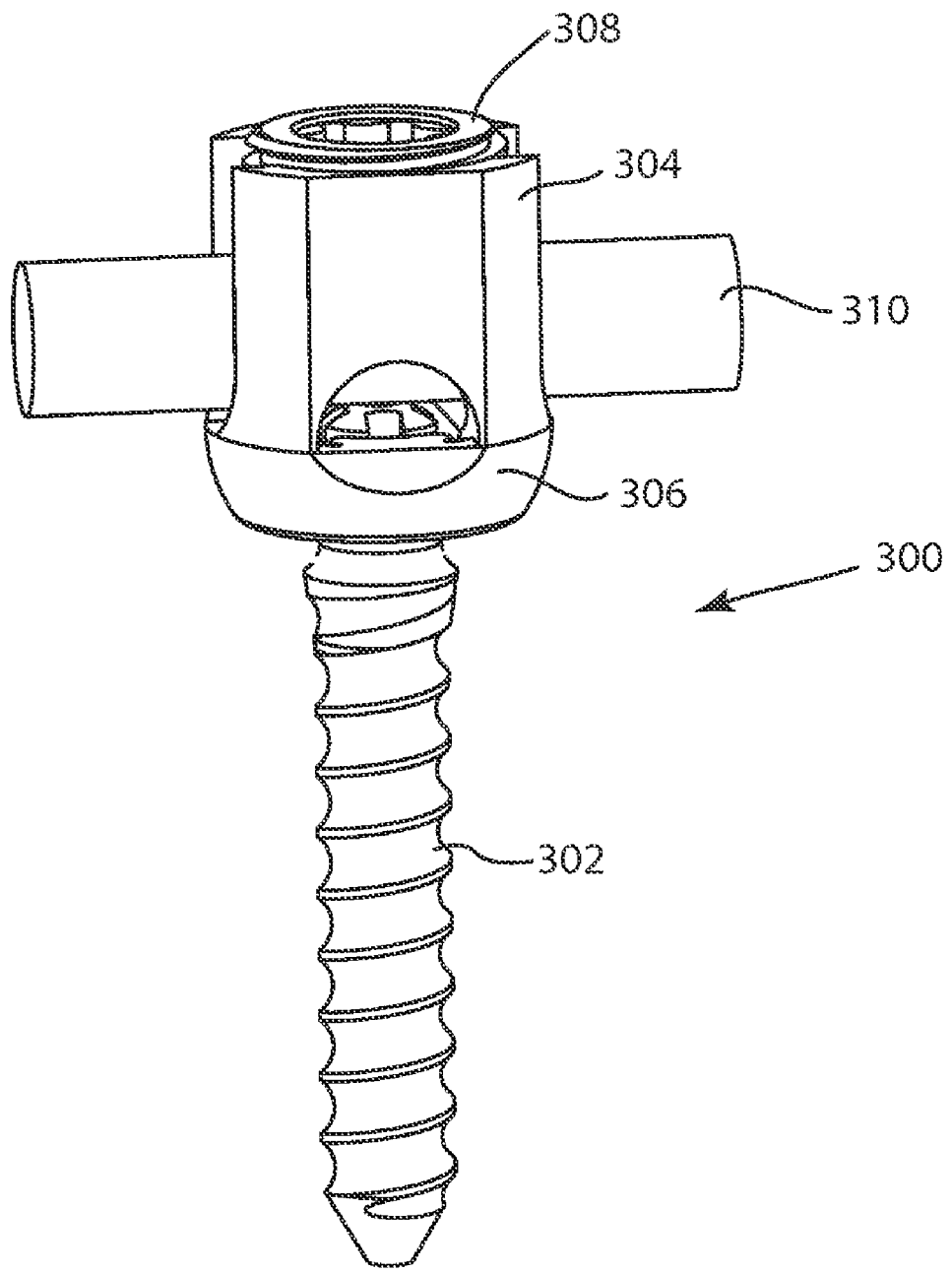
FIG. 14 illustrates a perspective view of an alternative embodiment of a bone anchor assembly and a spinal rod clamped in the bone anchor assembly, the bone anchor assembly comprising a bone anchor, a coupling head, a compression member and a collar.
Figure 15A:
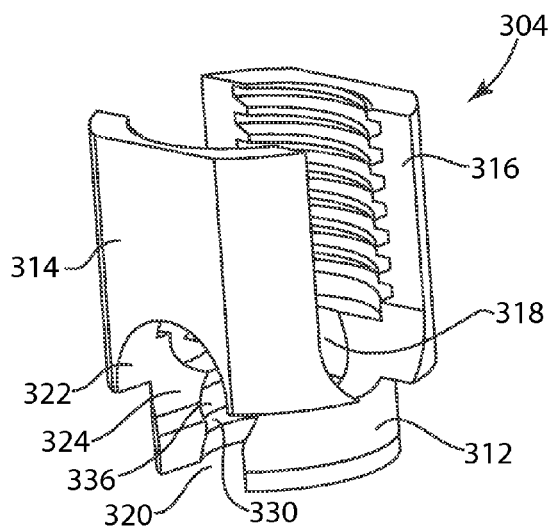
FIG. 15A illustrates a perspective view of the coupling head of FIG. 14.
Figure 15B:
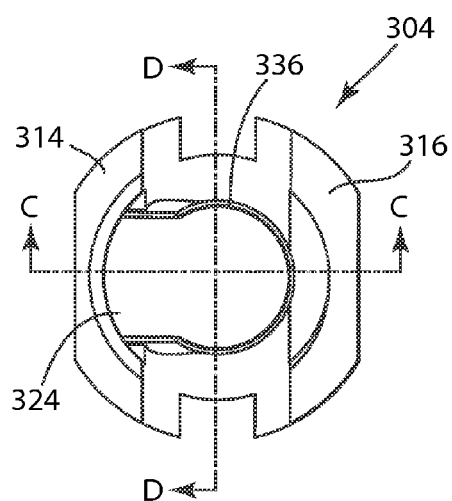
FIG. 15B illustrates a posterior view of the coupling head of FIG. 14.
Figure 15C:
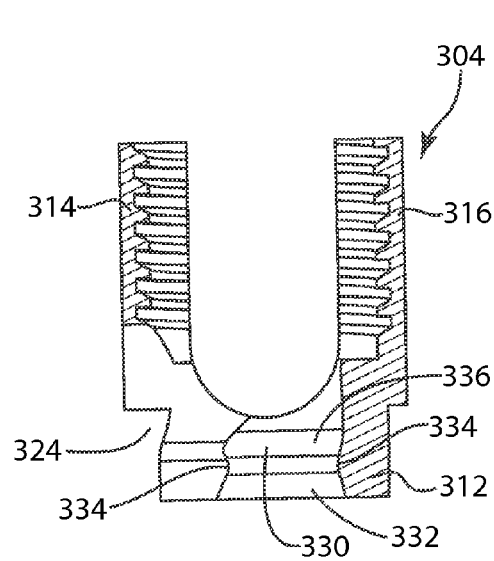
FIG. 15C illustrates a cross-sectional view of the coupling head of FIG. 14.
Figure 15D:
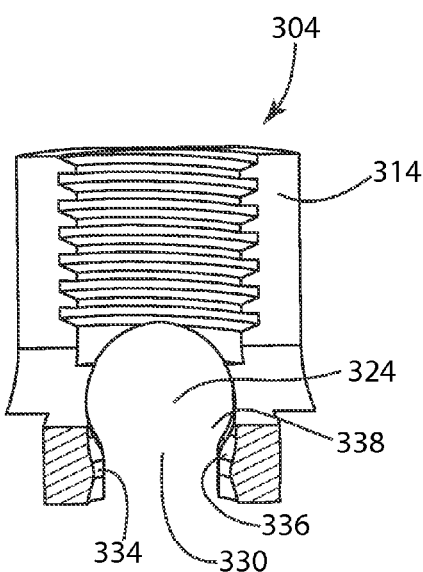
FIG. 15D illustrates a cross-sectional view of the coupling head of FIG. 14.

Referring to FIG. 14, a bone anchor assembly 300 is shown rigidly coupled with a spinal rod 310. Bone anchor assembly 300 comprises a bone anchor 302, a coupling head 304, a collar 306 and a compression element which is a set screw 308. Bone anchor 302 is configured to be anchored in a pedicle of a vertebra, or in another bone. Coupling head 304 is shaped to couple with bone anchor 302, and is shaped to receive a spinal rod 210 or other elongated rod-like member. Collar 306 may assist in retaining bone anchor 302 within the coupling head 304 and provide additional structural support to the coupling head 304. Set screw 308 is configured to be actuated to engage with the coupling head 304 to provide force on the spinal rod 310 and in turn the bone anchor 302, to lock out polyaxial motion between the bone anchor 302 and the coupling head 304, and to fix the position of the spinal rod 310 relative to the assembly 300.

Coupling head 304 is shown in greater detail in FIGS. 15A-D. Coupling head 304 is generally tulip-shaped, and comprises a semi-circular base portion 312, a first support wall 314 and a second support wall 316 positioned generally opposite the first support wall. A channel 318 shaped to receive the spinal rod 310 is positioned between the first and second support walls 314, 316. The base portion 312 is not fully circular but discontinuous, comprising a gap 320. Proximal to and continuous with the gap 320, a cutout 322 is formed in a portion of the first support wall 314. Together, the gap 320 and cutout 322 form a keyhole-shaped slot 324 sized to allow passage of a proximal end of the bone anchor 302. In the embodiment depicted in FIGS. 15A-D, the slot 324 is perpendicular to the channel 318; however in other embodiments of the invention the slot may be parallel, oblique or at another orientation relative to the channel, and may extend partway or all the way through the coupling head. Additionally, the slot 324 may comprise other shapes such as rectangular or circular, among others.

A bore 330 extends through the base portion 312, lined by a bore wall 332. A ridge 334 protruding from the bore wall defines a minimum diameter of the bore 330. Proximal to the ridge 334, a semispherical seat 336 encircles the bore, and is sized to retain a head portion of the bone anchor 302. A spherical cavity 338 sized and shaped to receive the head portion of the bone anchor is proximal to the semispherical seat 336. The slot 324 is in a transverse position relative to the bore 330, allowing side-loading of the bone anchor 302 into the bore.

Figure 16:
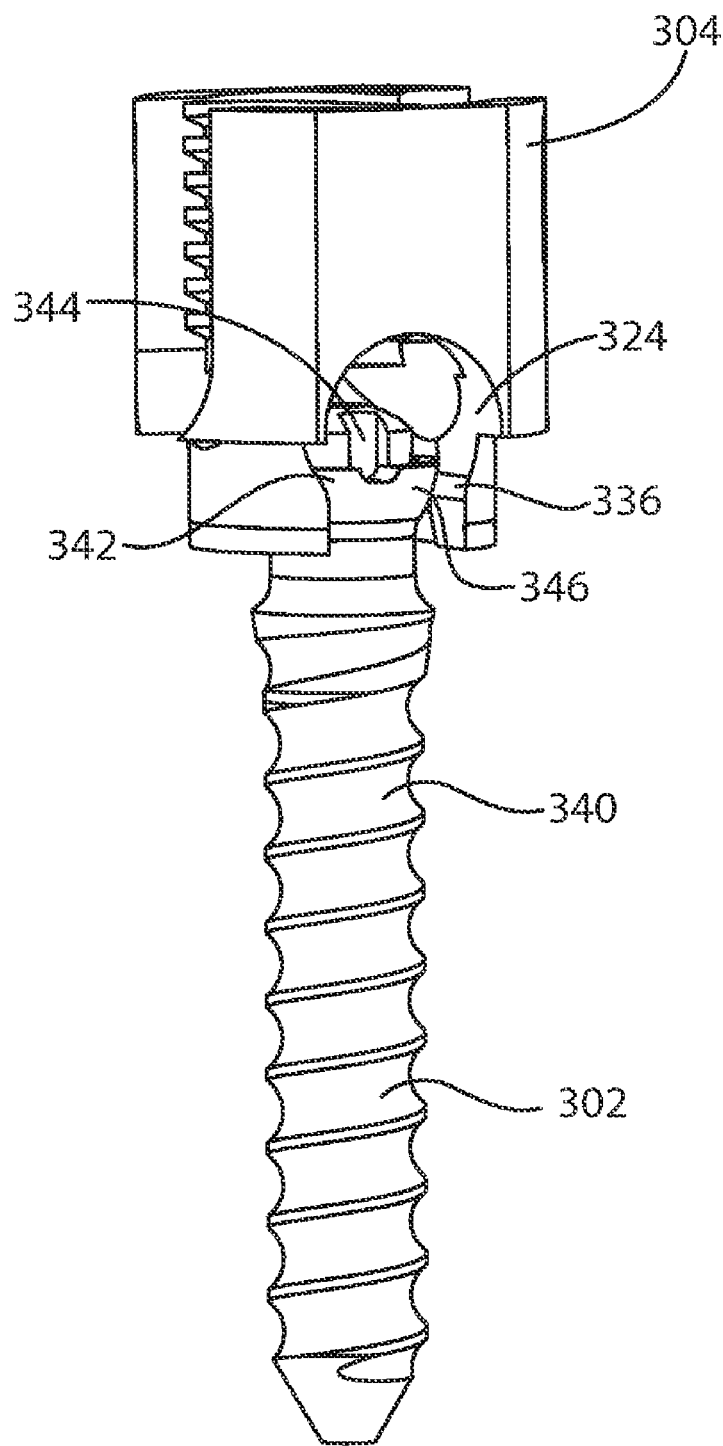
FIG. 16 illustrates a perspective view of the bone anchor and coupling head of FIG. 14, coupled together.

Referring to FIG. 16, the bone anchor 302 may be coupled with the coupling head 304. The bone anchor 302 comprises a threaded portion 340 and a head portion 342. The head portion 342 is semi-spherical and may comprise a plurality of driving features 344 and a semispherical shoulder 346. The bone anchor 302 may be formed as one piece or may comprise head and threaded portions which have been permanently joined together. The bone-anchor 302 may be side-loaded into the coupling head 304 with the head portion 342 guided through the slot 324, and the coupling head 304 and bone anchor 302 may be polyaxially adjusted relative to one another, such that the semispherical shoulder 346 of the head portion is able to rest at any of a plurality of relative orientations between the semispherical shoulder 346 and the semispherical seat 336.

Because the bone anchor 302 may be side-loaded into the coupling head 304 and need not be top-loaded, a maximum diameter of the head portion 342 may be less than a maximum diameter of the threaded portion 340. Similarly, the maximum diameter of the threaded portion 340 may be greater than a minimum diameter of the bore 330. The maximum diameter of the head portion 342 may be greater than the minimum diameter of the bore 330. Also, a maximum diameter of the spherical cavity 338 may be less than the maximum diameter of the threaded portion 340.

Once the bone anchor 302 has been loaded into the coupling head 304, the collar 306 may be coupled to the base portion 312 of the coupling head 304, to further retain the bone anchor 302. The collar may be further secured by press-fitting, threads, welding, or other means. The collar 306 is only one of many different retention members that may be used to keep the bone anchor 302 in place. If desired, such retention members may have features designed to interlock with or otherwise engage corresponding features of the coupling head 304. The collar 306 has a shape that generally complements that of the coupling head 304 to complete the interior wall of the bore 330.

Figure 17A:
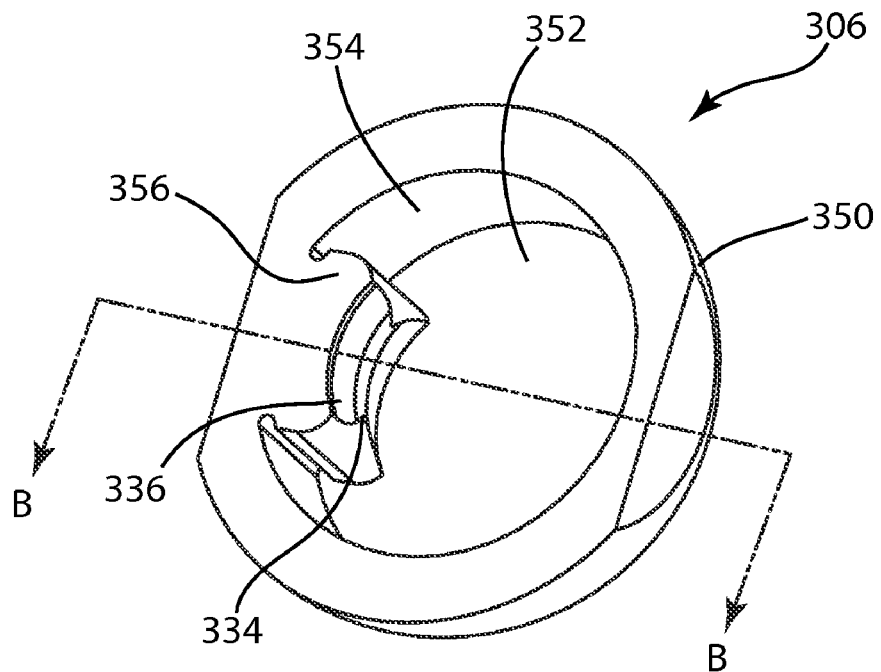
FIG. 17A illustrates a perspective view of the collar of FIG. 14.
Figure 17B:
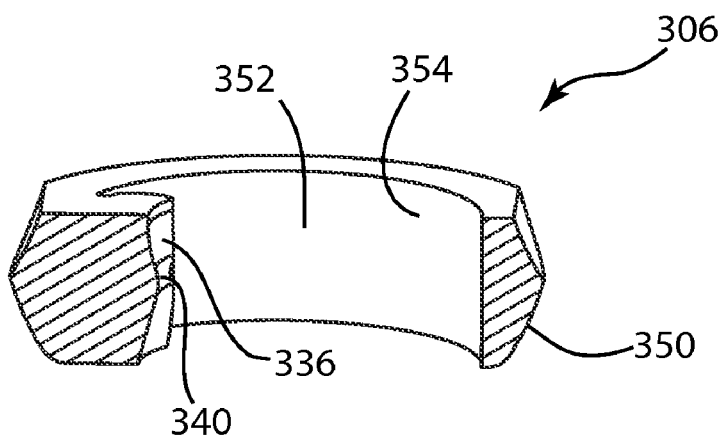
FIG. 17B illustrates a cross-sectional view of the collar of FIG. 17A.

Referring to FIGS. 17A and 17B, collar 306 is generally ring-shaped. An outer wall 350 of the collar 306 may be rounded and/or chamfered or otherwise shaped to attain a preferred profile. A collar bore 352 extends through the collar, the collar bore 352 having an inner bore wall 354. A projection 356 which protrudes inwardly from the inner bore wall 354 is shaped to fill the gap 320 in the coupling head 304 (not shown) when the collar 306 is secured to the coupling head 304. The projection 356 includes a portion of the semispherical seat 336 and the ridge 334.

Figure 18:
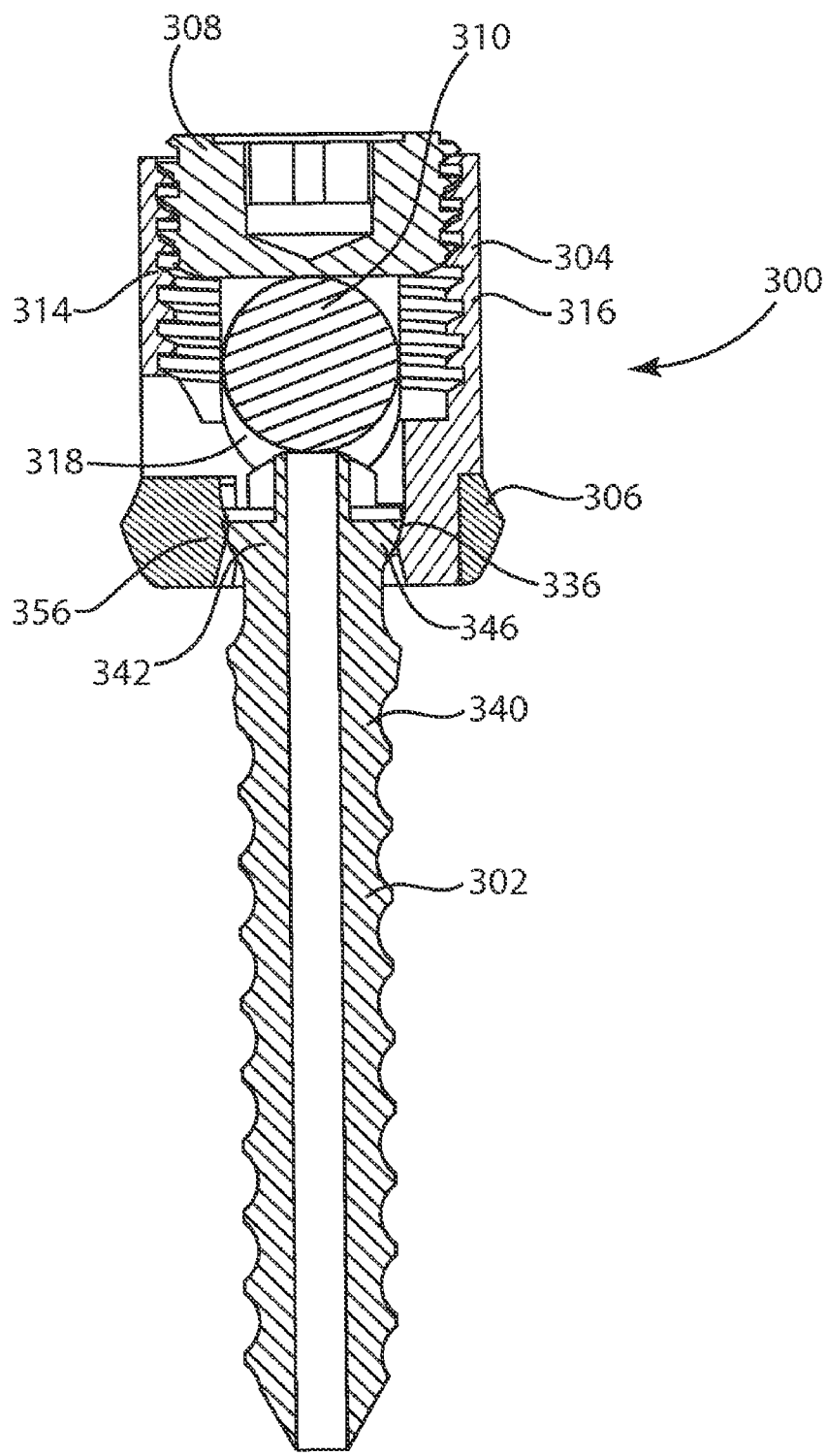
FIG. 18 illustrates a cross-sectional view of the bone anchor assembly and spinal rod of FIG. 14.

Referring to FIG. 18, a cross-sectional view of bone anchor assembly 300 assembled with spinal rod 310 is shown. Prior to implantation, bone anchor 302 may be side-loaded into coupling head 304, and collar 306 secured to coupling head 304. Bone anchor 302 may be driven into the pedicle of a vertebra, or another bone, using a driving tool (not shown). The coupling head 304 and collar 306 may be polyaxially rotated relative to the bone anchor 302 such that the semispherical shoulder 346 of the head portion 342 is able to rest at any of a plurality of relative orientations between the semispherical shoulder 346 and the semispherical seat 336. The spinal rod 310 or other elongated member may be top-loaded into the channel, and the set screw 308 threaded into the coupling head 304 to form a locking mechanism. As the set screw 308 is actuated, an inferior surface of the set screw is pressed against the implant rod 310, which in turn, transmits a force to the bone anchor head portion 342, which presses against the semispherical seat 336 in the coupling head 304 and collar 306. This action secures the rod in place while also locking the position/orientation of the rod coupling head relative to the bone anchor head.

Figure 19:
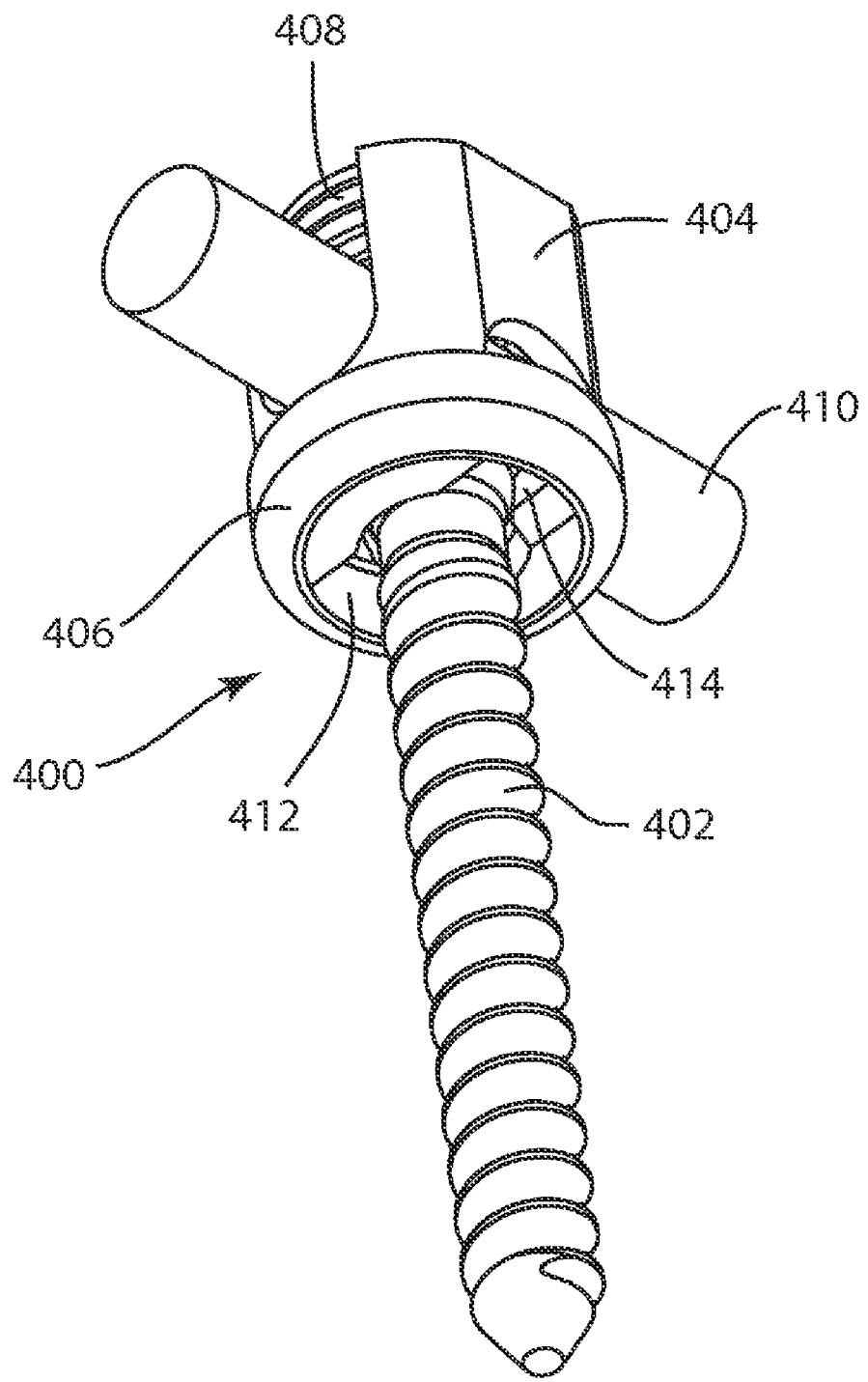
FIG. 19 illustrates a perspective view of an alternative embodiment of a bone anchor assembly and a spinal rod clamped in the bone anchor assembly, the bone anchor assembly comprising a bone anchor, a coupling head, a compression member and a collar.
Figure 20:
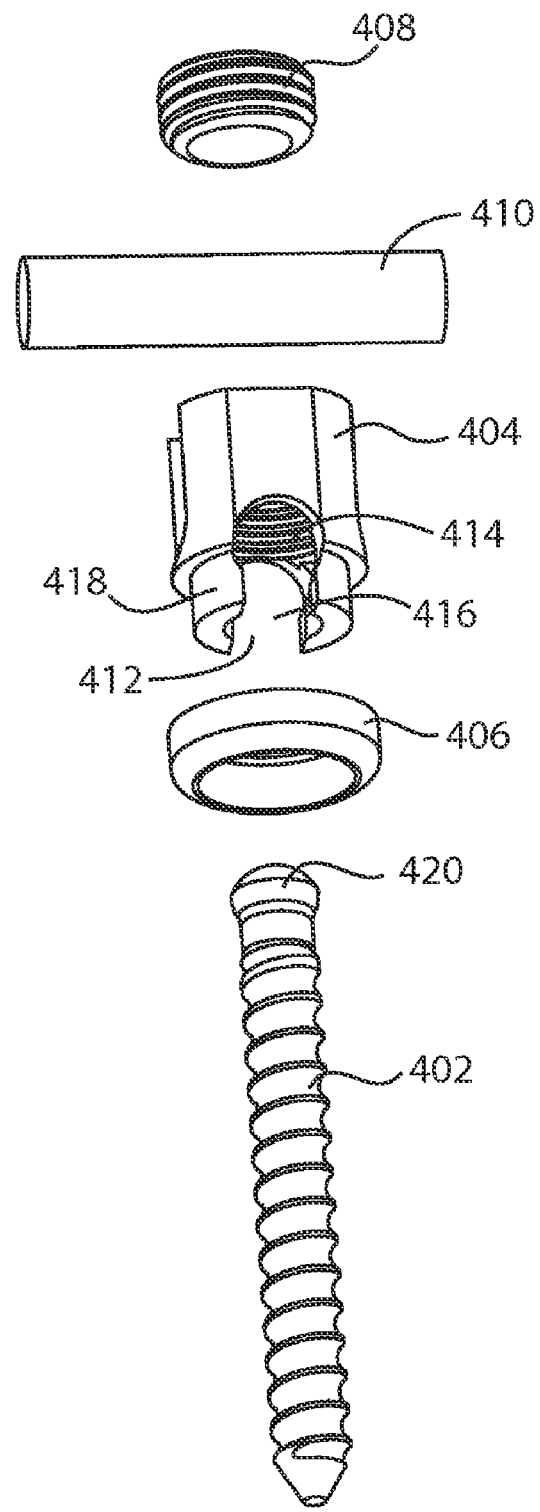
FIG. 20 illustrates an exploded perspective view of the bone anchor assembly and spinal rod of FIG. 19.

Referring to FIGS. 19 and 20, an alternative embodiment of a bone anchor assembly with a transverse opening that extends all the way across the coupling head is shown. Bone anchor assembly 400 is shown coupled with a spinal rod 410, and comprises a bone anchor 402, a coupling head 404, a collar 406, and a set screw 408. Coupling head 404 is similar to coupling head 304, except that coupling head 404 comprises two slots 412, 414 oriented opposite one another to form a single transverse opening 416 which extends all the way across a base portion 418 of the coupling head 404. As a result, a head portion 420 of bone anchor 402 may be inserted into the coupling head through either slot 412, 414 during assembly of the bone anchor assembly 400. Collar 406 is ring-shaped and sized to encircle the base portion 418 of the coupling head 404, to prevent withdrawal of bone anchor 402 from the coupling head.

Figure 21:
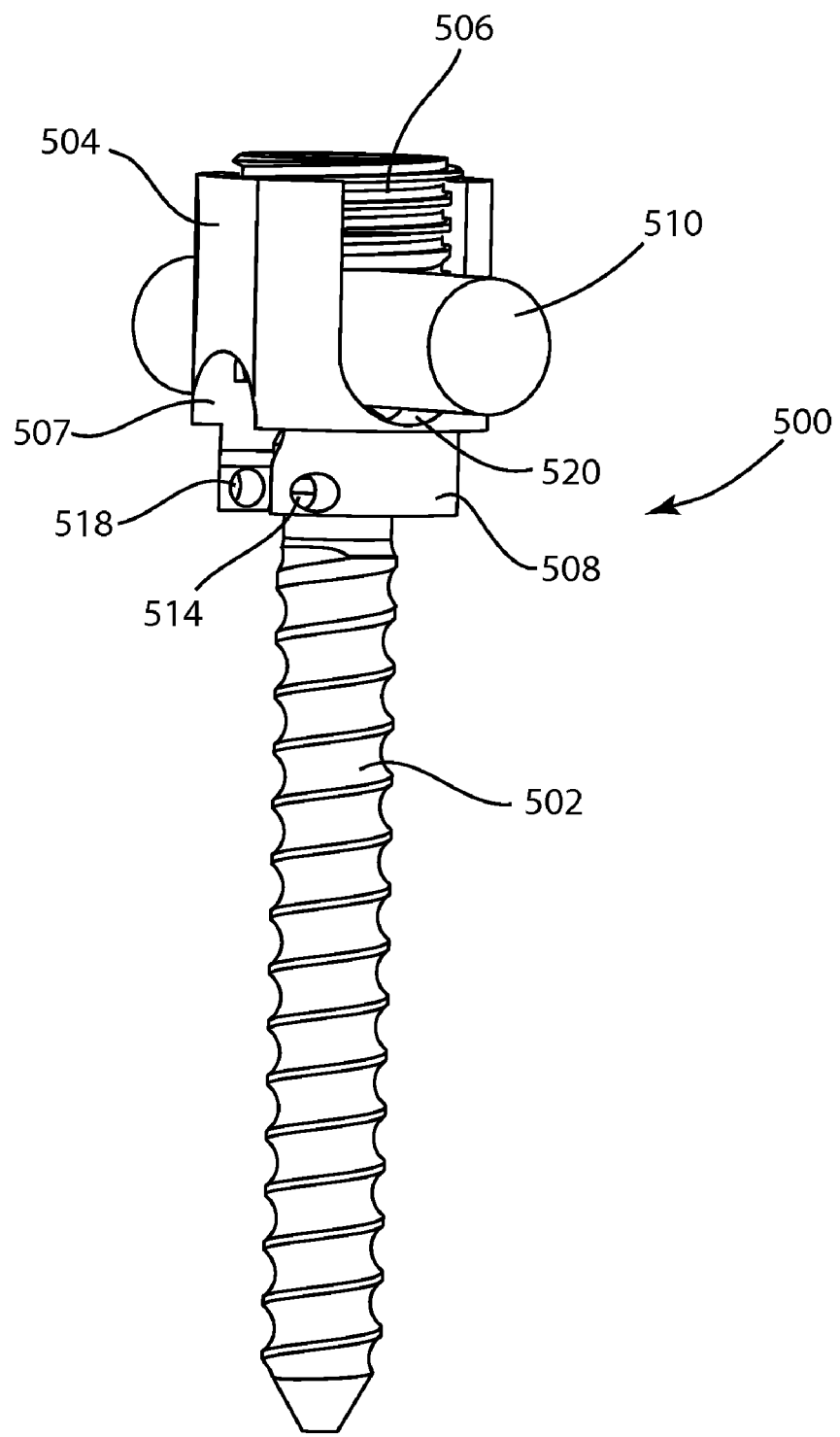
FIG. 21 illustrates a perspective view of an alternative embodiment of a bone anchor assembly and a spinal rod clamped in the bone anchor assembly, the bone anchor assembly comprising a bone anchor, a coupling head, and a compression member.
Figure 22:
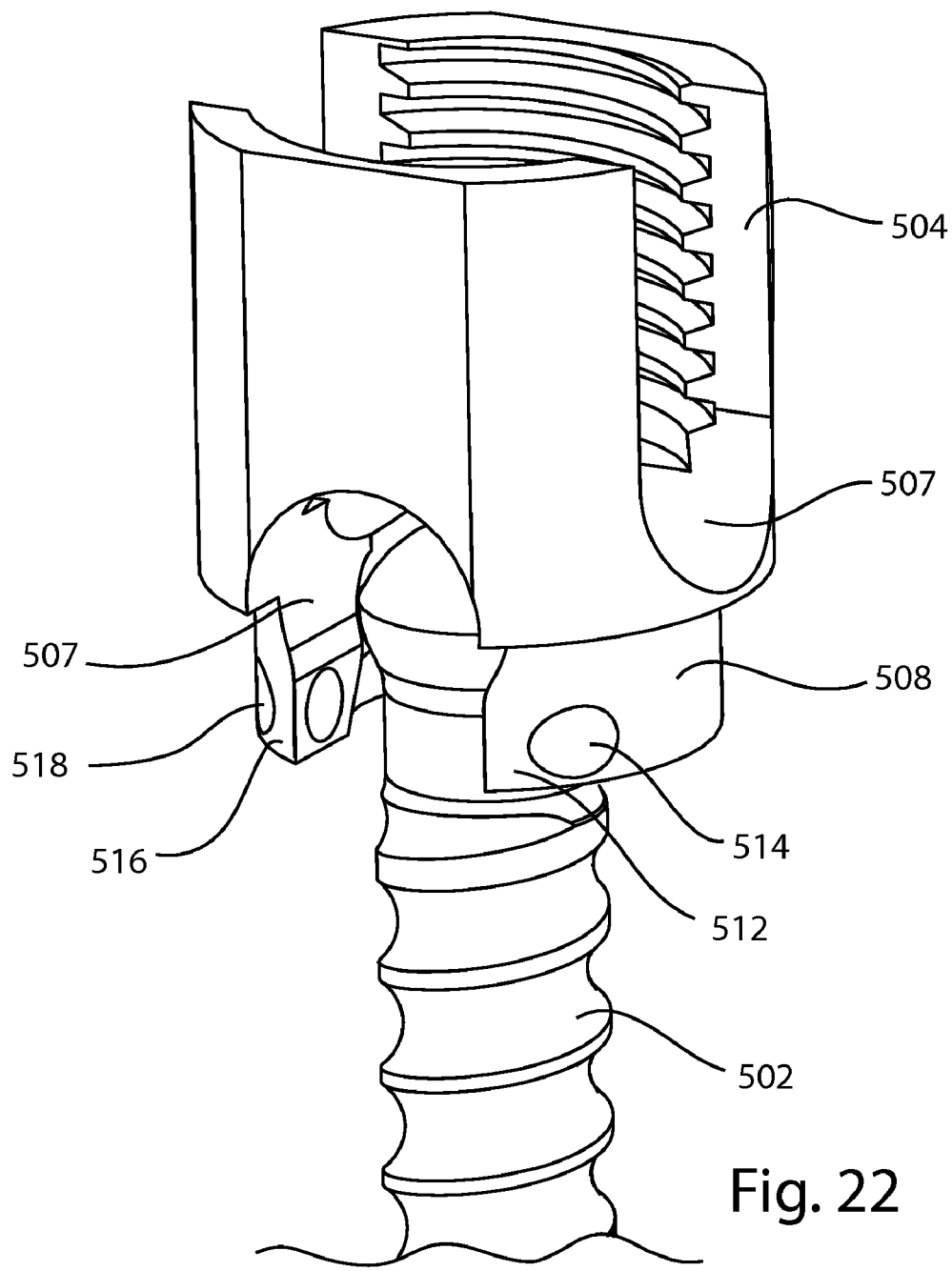
FIG. 22 illustrates an enlarged perspective view of the bone anchor and coupling head of FIG. 21.

Referring to FIGS. 21 and 22, an alternative embodiment of a bone anchor assembly with a base portion configured to accept a pin is shown. Bone anchor assembly 500 is shown coupled with a spinal rod 510, and comprises a bone anchor 502, a coupling head 504, and a set screw 506. The bone anchor 502 may be side-loaded into the coupling head 504 through a slot 507, similar to bone anchor assembly 300. The coupling head 504 has a semi-circular base portion 508. At a first end 512 of the base portion 508 is a first hole 514, and at a second end 516 of the base portion is a second hole 518. Holes 514, 518 are opposably oriented such that a pin (not shown) may extend through and between the holes to prevent withdrawal of the bone anchor 502. A channel 520, sized to receive spinal rod 510 extends across the coupling head 504 perpendicular to the slot 507. A collar (not shown) may optionally be secured onto the base portion to retain the pin and further retain the bone anchor.

Figure 23:
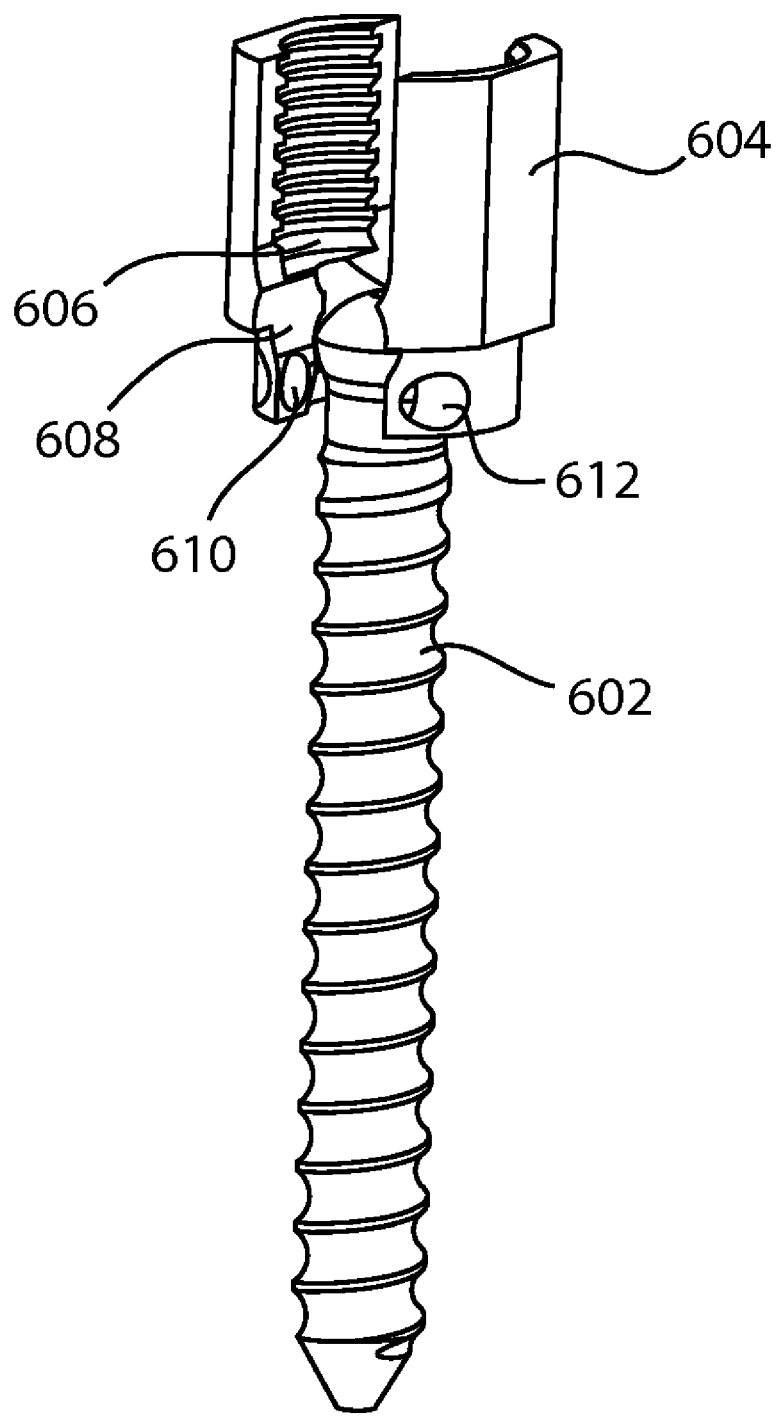
FIG. 23 illustrates a perspective view of a bone anchor and an alternative embodiment of a coupling head.

Referring to FIG. 23, a portion of another alternative embodiment of a bone anchor assembly is shown. Bone anchor 602 is shown received in coupling head 604. Coupling head 604 is similar to coupling head 504, with the exception that a channel 606 shaped to receive a spinal rod extends parallel to a slot 608. Coupling head 604 further comprises holes 610, 612 shaped to receive a pin (not shown) which may prevent withdrawal of the bone anchor 602 from the coupling head 604. A collar (not shown) such as collar 406 may optionally be secured onto the base portion to retain the pin and further retain the bone anchor.

Figure 24:
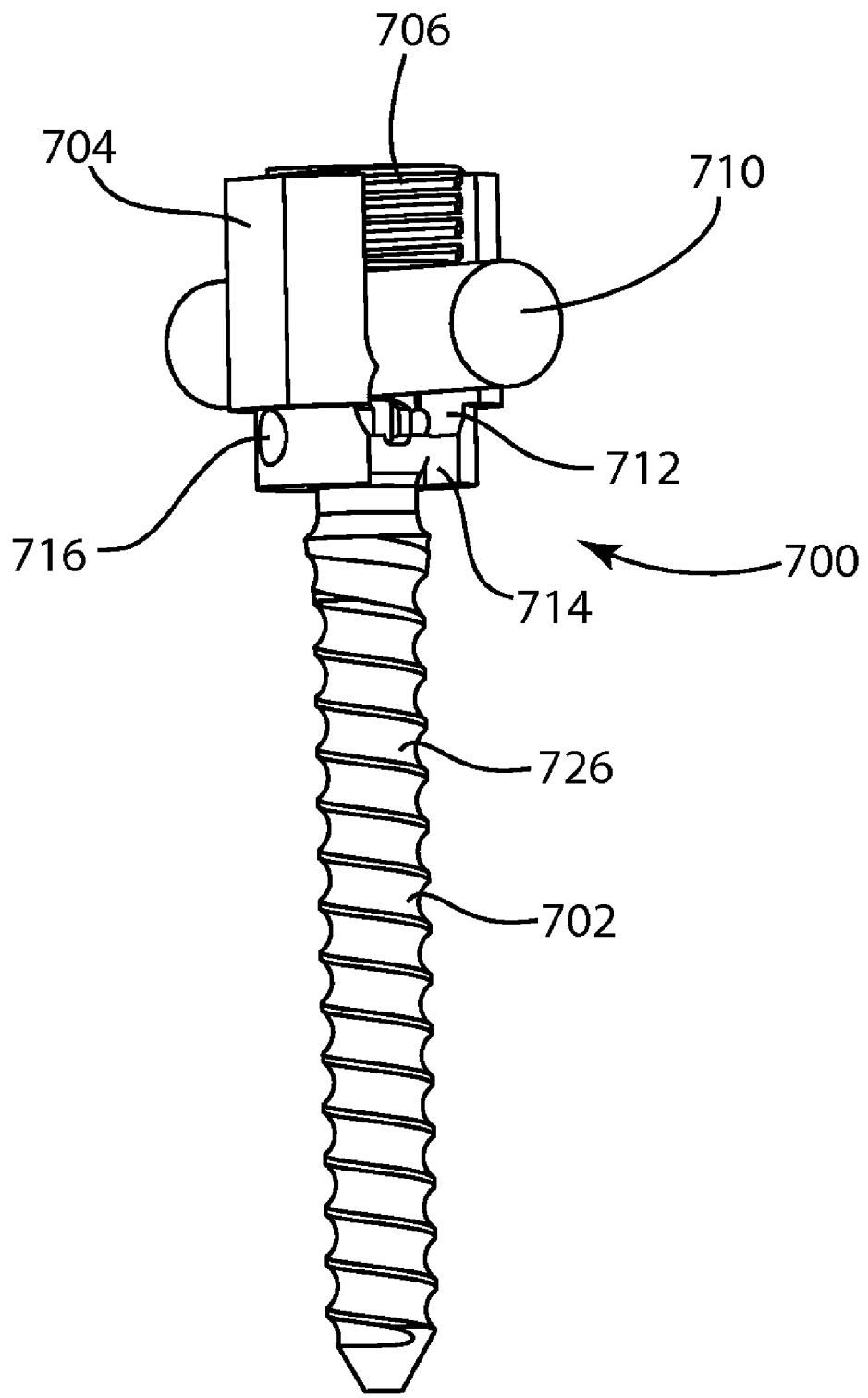
FIG. 24 illustrates a perspective view of an alternative embodiment of a bone anchor assembly and a spinal rod clamped in the bone anchor assembly, the bone anchor assembly comprising a bone anchor, a coupling head, and a compression member.
Figure 25:
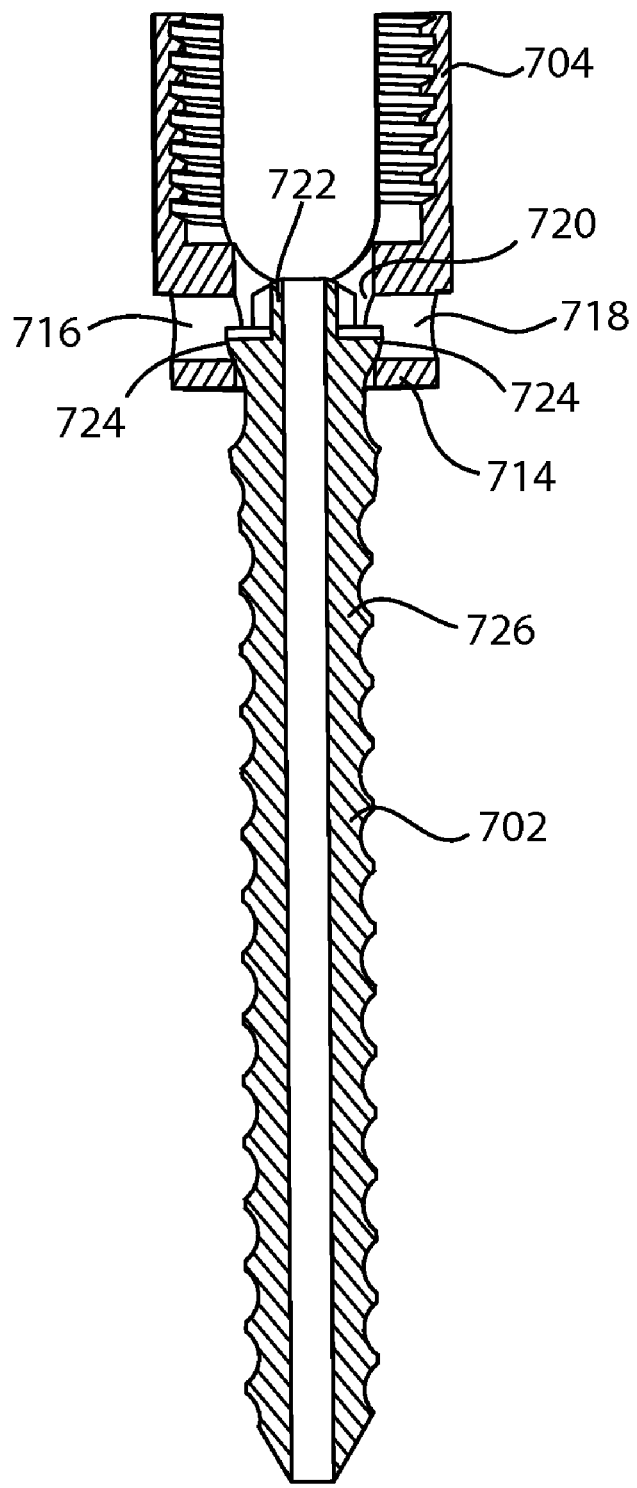
FIG. 25 illustrates a cross-sectional view of the coupling head and bone anchor of FIG. 24.

Referring to FIGS. 24 and 25, another alternative embodiment of a bone anchor assembly is shown. Bone anchor assembly 700 comprises a bone anchor 702, coupling head 704, set screw 706, and a collar (not shown) such as collar 406. Coupling head 704 comprises a slot 712 allowing the bone anchor 702 to be side-loaded into the coupling head. A base portion 714 comprises a first hole 716 and a second hole 718 located on opposing side of the base portion, each hole extending through the base portion and in communication with a spherical cavity 720. A head portion 722 of the bone anchor 702 may be side-loaded through the slot 712 into the spherical cavity 720. A semispherical shoulder 724 of the head portion 722 may be engaged in the holes 716, 718, retaining the head portion 722 in the semispherical cavity and allowing a threaded portion 726 to extend distal of the coupling head 704. The collar is secured around the base portion 714 to further retain the bone anchor 702.

Bone anchor assemblies 400, 500, 600 and 700 may be assembled and implanted similarly to the method described for bone anchor assembly 300. In all four assemblies, the bone anchor may be side loaded into the coupling head. A collar and/or pin may be secured to the coupling head to prevent withdrawal of the bone anchor. The bone anchor may be anchored into a bone, and the coupling head and bone anchor polyaxially rotated relative to one another to a preferred orientation. A spinal rod may be loaded into the channel of the coupling head in a preferred position, and the set screw fastened into the coupling head. As the set screw is actuated, it presses on the spinal rod, which in turn presses on the head of the bone anchor, seating the bone anchor head against the coupling head at the preferred orientation. The position of the spinal rod and the position and orientation of the bone anchor relative to the coupling head are thus locked down.

The present invention may be embodied in other specific forms without departing from its spirit or essential characteristics. For example, above are described various alternative examples of pedicle screw and rod coupling systems for providing spinal support. It is appreciated that various features of the above-described examples can be mixed and matched to form a variety of other alternatives. It is also appreciated that this system should not be limited creating access to the intervertebral space. This arcuate access system may be used to obtain access to any portion of the spine. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A bone anchor assembly securable to an elongated member, the bone anchor assembly comprising:
 a bone screw comprising a threaded portion and a head portion;
 a coupling member comprising a first bore, the first bore comprising a seat shaped to polyaxially adjustably receive the head portion, a second bore, and a channel proximally positioned relative to the first bore and in direct communication with the first bore, wherein the channel is shaped to receive the elongated member; and
 a locking mechanism actuatable to lock the elongated member in a fixed position relative to the channel, the locking mechanism comprising a locking member and an engagement member shaped to slide transverse to the locking member in response to actuation of the locking member to retain the elongated member, wherein the locking member is actuatable within the engagement member and is engaged with the second bore;

wherein the engagement member is a wedge member comprising a first oblique surface, wherein the coupling member further comprises a second oblique surface oriented oblique to the first bore, and wherein the first oblique surface is urged transversely along the second oblique surface in response to actuation of the locking member, wherein the coupling member is J-shaped comprising a first wall and a second wall, the second wall including the second oblique surface and being shorter and wider than the first wall, wherein the second bore is located in the second wall, and wherein the engagement member is positionable on the second oblique surface of the second wall.

2. The bone anchor assembly of claim 1, wherein the second bore is isolated from the first bore and parallel to the first bore.

3. The bone anchor assembly of claim 1, wherein a maximum diameter of the threaded portion is greater than a minimum diameter of the first bore.

4. The bone anchor assembly of claim 1, wherein the head portion comprises a semispherical shoulder, wherein the seat of the first bore comprises a semispherical seat against which the semispherical shoulder of the head portion is able to rest at any of a plurality of relative orientations between the semispherical shoulder and the semispherical seat.

5. The bone anchor assembly of claim 1, wherein the engagement member is shaped to be urged transversely against the elongated member in response to actuation of the locking member within the second bore.

6. The bone anchor assembly of claim 1, wherein the elongated member comprises an attachment portion shaped to be received by the coupling member.

7. The bone anchor assembly of claim 1, wherein the head portion and the threaded portion are formed as separate pieces, each of which comprises a fitting feature, wherein the fitting features mate together to facilitate joining of the head portion and the threaded portion after the head portion is received by the coupling member.

8. The bone anchor assembly of claim 1, wherein a maximum diameter of the head portion is less than a maximum diameter of the threaded portion.

9. The bone anchor assembly of claim 1, wherein the locking mechanism is offset from the channel.

10. The bone anchor assembly of claim 1, wherein the locking member is a screw.

11. The bone anchor assembly of claim 1, wherein the locking mechanism is further configured to lock the position of the bone screw relative to the coupling member.

12. A method of securing an elongated member to a bone anchor assembly comprising a coupling member, a bone screw, and a locking member; the method comprising:
providing the bone anchor assembly of claim 1;
securing the threaded portion of the bone screw in a bone;
positioning the elongated member in the channel of the coupling member;
adjusting an orientation of the bone screw polyaxially relative to the coupling member such that the head portion of the bone screw rotates within the first bore of the coupling member; and
actuating the locking member within the second bore of the coupling member to lock the elongated member in a fixed position relative to the assembly and restrict polyaxial adjustability of the bone screw relative to the coupling member.

13. The method of claim 12, wherein the second bore is isolated from the first bore and parallel to the first bore.

14. The method of claim 12, wherein a maximum diameter of the threaded portion is greater than a minimum diameter of the first bore.

15. The method of claim 12, wherein the head portion comprises a semispherical shoulder, wherein the first bore comprises a corresponding semispherical seat, wherein adjusting an orientation of the bone screw polyaxially relative to the coupling member comprises positioning the semispherical shoulder of the head portion at any of a plurality of relative orientations between the semispherical shoulder and the semispherical seat.

16. The method of claim 12, wherein actuating the locking member within a second bore of the coupling member to lock the elongated member in a fixed position relative to the assembly further comprises urging the engagement member transversely against the elongated member.

17. The method of claim 16, wherein urging the engagement member transversely against the elongated member further comprises urging the first oblique surface of the engagement member along the second oblique surface of the coupling member.

18. A method of securing an elongated member to a bone anchor assembly comprising a coupling member, a bone screw, and a locking mechanism; the method comprising:
providing the bone anchor assembly of claim 1;
securing the threaded portion of the bone screw in a bone;
positioning the elongated member in the channel of the coupling member;
adjusting an orientation of the bone screw relative to the coupling member such that the head portion of the bone screw rotates within the first bore of the coupling member; and
actuating the locking mechanism to lock the elongated member in a fixed position relative to the channel;
wherein actuating the locking mechanism comprises urging the engagement member of the locking mechanism to slide transverse to the locking member of the locking mechanism to retain the elongated member.

19. The method of claim 18, wherein actuating the locking mechanism further comprises locking a position of the bone screw relative to the coupling member to restrict polyaxial adjustability of the bone screw relative to the coupling member.

20. The method of claim 18, wherein actuating the locking mechanism further comprises actuating the locking member to urge the engagement member of the locking mechanism to slide transverse to the locking member.

21. The method of claim 18, wherein urging the engagement member to slide transverse to the locking member further comprises urging the first oblique surface of the engagement member to slide along the second oblique surface of the coupling member, wherein the second oblique surface is oriented oblique to the first bore.

22. The method of claim 18, wherein actuating the locking mechanism to lock the elongated member in a fixed position relative to the channel comprises actuating the locking member within the second bore.

* * * * *